(12) United States Patent
Jiang et al.

(10) Patent No.: US 9,005,661 B2
(45) Date of Patent: Apr. 14, 2015

(54) OSMOTIC PUMP CONTROLLED RELEASE TABLET AND PREPARATION METHOD THEREOF

(75) Inventors: Qingwei Jiang, Beijing (CN); Weifeng Yi, Beijing (CN); Quanzhi Liu, Beijing (CN); Wenbin Yang, Beijing (CN); Junli Zheng, Beijing (CN)

(73) Assignee: Beijing Team Hospital Management Co., Ltd., Beijing (CN)

( * ) Notice: Subject to any disclaimer, the term of this patent is extended or adjusted under 35 U.S.C. 154(b) by 0 days.

(21) Appl. No.: 13/496,454

(22) PCT Filed: Apr. 29, 2010

(86) PCT No.: PCT/CN2010/072316
§ 371 (c)(1),
(2), (4) Date: Mar. 15, 2012

(87) PCT Pub. No.: WO2011/032386
PCT Pub. Date: Mar. 24, 2011

(65) Prior Publication Data
US 2012/0171287 A1      Jul. 5, 2012

(30) Foreign Application Priority Data

Sep. 15, 2009   (CN) .......................... 2009 1 0177529

(51) Int. Cl.
*A61K 9/00* (2006.01)
(52) U.S. Cl.
CPC ................................... *A61K 9/0004* (2013.01)
(58) Field of Classification Search
CPC ........ A61K 9/004; A61K 47/32; A61K 47/38
See application file for complete search history.

(56) References Cited

U.S. PATENT DOCUMENTS

| 4,455,143 | A | 6/1984 | Theeuwes et al. |
| 5,413,572 | A * | 5/1995 | Wong et al. ................ 604/892.1 |
| 6,350,471 | B1 | 2/2002 | Seth |
| 2003/0056896 | A1 | 3/2003 | Jao et al. |

FOREIGN PATENT DOCUMENTS

| CN | 101337074 | 1/2009 |
| JP | 58-162518 | 9/1983 |
| JP | 6-500774 | 3/1992 |
| JP | 2008-508317 | 3/2008 |
| WO | WO 92/04011 | 3/1992 |
| WO | WO 01/56543 A1 | 8/2001 |
| WO | WO 2006/015294 | 2/2006 |

OTHER PUBLICATIONS

Verma, Rajan K, et al., "Development and evaluation of osmotically controlled oral drug delivery system of glipizide", European Journal of Pharmaceutics and Biopharmaceutics, 2004, vol. 57, Issue 3, pp. 513-525, ISSN: 09396411.
PCT/CN2010/072316, Aug. 5, 2010, International Search Report.
European Search Report dated Mar. 31, 2014 for European Application No. 10816590.3 (5 pgs).

* cited by examiner

*Primary Examiner* — Susan Tran
*Assistant Examiner* — Jessica Worsham
(74) *Attorney, Agent, or Firm* — Workman Nydegger

(57) ABSTRACT

An osmotic pump controlled release tablet and the preparation method thereof are disclosed. The osmotic pump controlled release tablet is composed of tablet core, semipermeable membrane and optional film coating. The material of said semipermeable membrane is composed of ethyl cellulose and povidone in the ratio of 1:1~1:4 by weight. Said tablet core comprises drug containing layer and push layer. The osmotic pump controlled release tablet also characterizes in that; (1) the angle $\theta_1$ formed by the outer curved surface of the drug containing layer and the lateral surface is 120°-180°; and/or (2) the ratio of $L_1$ to r is 0.27-1.0, wherein $L_1$ is the vertical distance from the central vertex of the outer curved surface of the drug containing layer to the plane formed by the intersection line between the outer curved surface of the drug containing layer and the lateral surface, and r is the radius of the tablet core.

6 Claims, 2 Drawing Sheets

OSMOTIC PUMP CONTROLLED RELEASE TABLET AND PREPARATION METHOD THEREOF

CROSS REFERENCE TO RELATED APPLICATIONS

This application is a U.S. Nationalization of PCT Application Number PCT/CN2010/072316, filed on Apr. 29, 2010, which claims priority to Chinese Patent Application No. 200910177529.X, filed on Sep. 15, 2009, the entireties of which are incorporated herein by reference.

FIELD OF INVENTION

The present invention relates to an osmotic pump controlled release tablet and preparation method thereof and belongs to the field of pharmaceutical preparations.

BACKGROUND OF THE INVENTION

Osmotic pump controlled release preparations are typical representatives of sunstained and controlled release preparations, characterized in that they use osmotic pressure as the driving force for drug release and follow the zero-order release kinetics. Osmotic pump controlled release preparations have become a hot topic of research and development all over the world. Among them, osmotic pump controlled release tablet is the most common dosage form of oral osmotic pump controlled release preparations.

Based on the structural characteristics, oral osmotic pump preparations can be divided into two types: mono-compartment osmotic pumps and multi-compartment osmotic pumps. The mono-compartment osmotic pumps are generally used for water-soluble drugs, and consist of a tablet core and a coating film. The tablet core consists of a drug and a high-permeability material. The coating film is commonly a rigid semipermeable membrane formed by a polymer material such as cellulose acetate or ethyl cellulose, and one or more releasing orifice(s) are usually drilled by laser or other means (such as mechanical force) on the semipermeable membrane and used as the output channel of drugs. When being used, the high-permeability material in the tablet core produces high osmotic pressure after being dissolved, then a static pressure difference between inside and outside of the semipermeable membrane is formed. Thus, under this pressure difference, a drug suspension or solution outflows from the tablet, while external water inflows into the tablet, moreover, the inflowing speed of water is equal to the outflowing speed of the drug suspension or solution. Mono-compartment osmotic pump controlled release tablets are mainly suitable for water-soluble drugs, and not applicable to water-insoluble drugs, especially poorly water-insoluble drugs. In addition, due to the limitation of structure, mono-compartment osmotic pumps will no longer release drugs at a constant rate at the late stage of release, and the osmotic pressures are reduced and may even cause drug residue in preparations, like ordinary sustained-release formulations. Due to the above-mentioned problems present in mono-compartment osmotic pumps, multi-compartment osmotic pumps have subsequently been developed.

Multi-compartment osmotic pumps consist of at least two layers: a drug-containing layer and a push layer, which constitute a drug compartment and a force compartment respectively. The most widely used osmotic pumps are double-compartment osmotic pumps. The drug-containing layer consists of a drug, a penetration-promoting agent and a suspending agent. The push layer consists of one or more swellable polymer materials and a penetration-promoting agent. When being used, water enters into the tablet core through the semipermeable membrane, resulting in the drug-containing layer is softened by absorbing water, meanwhile, the polymer material in the push layer swells by absorbing water and squeeze the drug compartment, so that drugs are released from the releasing orifices. A constant osmotic pressure will keep a constant speed of water entering into the tablet core, thereby keep a constant swelling speed of the polymer material by absorbing water in order to maintain the persistence of a constant osmotic pressure and achieve a constant drug release rate. In addition, the drug, whether existing in a solution or a suspension, can be squeezed out of the semipermeable membrane by the swelled push layer. However, mono-compartment osmotic pump controlled release tablets will cause the penetration-promoting agent and the drug being separated from each other during the delivery of poorly water-soluble drugs, thereby resulting in drug residue in the tablet core. Thus, multi-compartment osmotic pumps are applicable to all types of drugs, and they have more obvious advantages in the aspect of deliverying poorly water-soluble drugs compared with mono-compartment osmotic pump controlled release tablets. At present, successful osmotic pump preparations on the market are mostly double-compartment osmotic pump tablets. Successful examples include Nifedipine double-compartment osmotic pump tablets (Adalat®) developed by Bayer Company of Germany and Verapamil hydrochloride controlled release tablets designed and developed by Alza company of the United States based on the Nifedipine double-compartment osmotic pump tablets. At present, the technique of double-compartment osmotic pump preparations is the most mature and appropriate method for industrial method for preparing poorly water-insoluble drugs into osmotic pump preparations. Multiple-compartment (more than two compartments) osmotic pump controlled release tablets, for example, three-compartment osmotic pump controlled release tablets, are seldom used since their preparation processes are very onerous and they do not have apparent advantages in performance over double-compartment osmotic pumps. The important osmotic pump controlled release tablets on the market in the foreign countries are shown in Table 1.

TABLE 1 important osmotic pump controlled release tablets on the market in foreign countries

| No. | Trade name | active ingredient | The material of semi-permeable membrane | developed by |
|---|---|---|---|---|
| 1 | Acutrim | Phenylpropanolamine | CA | Alza |
| 2 | Alpress LP | Prazosin | CA | Alza |
| 3 | Cardura XL | Doxazosin Mesylate | CA | Alza |
| 4 | Covera HS | Verapamil | CA | Alza |
| 5 | Concenta | Methylphenidate | CA | Alza |
| 6 | Ditropphan XL | Oxybutynin Chloride | CA | Alza |
| 7 | DynaCirc CR | Isradipine | CA | Alza |
| 8 | Efidac 24 Pseudoephedrine | Norpseudoephedrine | CA | Alza |
| 9 | Efidac 24 chlorpheniramine | Chlorpheniramine | CA | Alza |

TABLE 1-continued important osmotic pump controlled release tablets
on the market in foreign countries

| No. | Trade name | active ingredient | The material of semi-permeable membrane | developed by |
|---|---|---|---|---|
| 10 | Efidac 24 Brompheniramine& Pseudoephedrine | Brompheniramine and Norpseudo-ephedrine | CA | Alza |
| 11 | Glucotrol XL | Glipizide | CA | Alza |
| 12 | Procardia XL | Nifedipine | CA | Alza |
| 13 | Teczem | Enalapril and Diltiazem | CA | Merck& Hoechst Marion |
| 14 | Tiamate | Diltiazem | CA | Merck |
| 15 | Volmax | Salbutamol | CA | Alza |

Semipermeable membrane is very important for the control of drug release in oral osmotic pump formulations. It must meet the following requirments: (1) sufficient wet strength; (2) water can penetrate through it selectively, but solute can not penetrate through it; (3) biocompatible. Ideal semipermeable membrane should possesses the following characteristics:

(1) selective permeability: water can effectively enter the inside of the tablet core, and the permeation-active substances and drug inside of the tablet core can be effectively prevented from being released by diffusion through the semipermeable membrane;

(2) high strength and rigidity: it has a certain strength to prevent the membrane from breaking due to the internal static pressure difference or expansion of the tablet core so that the release behavior suddenly changes. If the semipermeable membrane has a certain tensile strength, the extrusion force produced by expansion of the push layer will be counteracted to some extent, so that the suddenly change of release behavior will be avoided;

(3) without aging: the semipermeable membrane does not age (i.e., components in the semipermeable membrane integrate with each other more and more closely) during storage, so that the permeability will not change and the stabilities of the samples will not reduce during storage; and (4) the semipermeable membrane must be transparent or translucent, thereby making it easy to identify the drug-containing layer (drug compartment) and the push layer (force compartment) when orifices are drilled by laser.

Cellulose acetate (CA) is most commonly used as a semipermeable membrane material. Other materials such as ethyl cellulose (EC) is also mentioned in literatures to be used as a film-coating of osmotic pumps. However, ethyl cellulose has poor water permeability, so it has not been used in the production of osmotic pump controlled release tablets (S. Rose and J. F. Nelson, Aust. J. Exp. Biol. Med. Sci., 1995, 33,415.). It can also be seen from Table 1, CA is used as a semipermeable membrane material in various important osmotic pump controlled release tablets on the market.

The semipermeable membrane made of different coating materials has different water permeability, which is related to the membrane penetration coefficient (k). The semipermeable membrane material now used is commonly cellulose acetate (CA), to which plasticizer is usually added to adjust the penetration rate thereof. Hydrophilic plasticizer polyethylene glycol (PEG) can increase the drug release rate, while hydrophobic plasticizer glycerol triacetate has an opposite effect.

For example, the semipermeable membrane of Procardia XL (Adalat®, nifedipine controlled release tablet) on the market was measured by differential scanning calorimetry (DSC) and compared with a single cellulose acetate membrane and a single PEG at the same time. It was found based on the melting endothermic peak that the combination of CA and PEG6000 was effected in the semipermeable membrane of Adalat to control drug release, wherein PEG plays a dual role as a plasticizer and a pore-forming agent.

We found that osmotic pump controlled release tablets prepared using common semipermeable membrane material at present (for example, cellulose acetate/polyethylene glycol) have a good release profile at a period of time after preparation, however, after being stored for a period of time, the release properties began to deteriorate. The longer the product is stored, the more obviously the release properties deteriorate. The release often reduces remarkably at the latter half of the validity period prescribed (usually two years or so), and even the drug can not be released at all after 2 years since production at factory. The reason is that PEG might plays two opposing roles of a plasticizer and a pore-forming agent at the same time, so hidden troubles are present for the storage stability of osmotic pump tablets. Since PEG has a plasticizing effect, it will combine with cellulose acetate constantly during the storage, thereby reducing the dissolution ratio in the release process. Reduced pore-forming effect results in decreased membrane permeability, so that the release becomes slow, popularly called physical aging. PEG with low molecular weight, due to its low melting point, the thermal stability thereof is even worse. Using diethyl phthalate as a plasticizer has the same problem. In order to overcome the release decline caused by physical aging, excessive feeding (namely, active ingredient of an amount of more than that calculated by the labelled amount is added during the preparation) is often required, in order to ensure the release in conformity of the requirement within the validity period.

For example, we found that when the influencing factors were examined by storing commercially available Glipizide controlled release tablets under the conditions of 40° C., 60° C., RH 75% and RH 92.5%, the results showed that the release were significantly decreased. In the membrane weight loss experiments, we found that the weight loss of membrane under each condition was significantly decreased relative to day 0 compared with samples that were not subjected to accelerated testing under the above conditions, suggesting that the membrane permeability was lowered, namely, in the above storage conditions, varying degrees of aging occurred in the semipermeable membrane.

Ethyl cellulose is a hydrophobic polymer material, which is widely used in sustained-release pellets. It is well known that the particle size of sustained-release pellets is generally in the range of 0.5-2 mm, so such a small particle size will inevitably lead to a very large surface area of release for a certain amount of products. Thus, for a water-soluble drug, a membrane with relatively smaller permeability has to be used to prepare a sustained-release preparation. Ethyl cellulose has a unique advantage in the field of sustained-release pellets due to its characteristics of small permeability, good film-forming property, and facilitating regulation of the release, and it can effectively control the drug release in the cases of small weight increase of coating. The active ingredient in sustained-release pellets mainly release in a dissolution-diffusion mode, which is suitable for water-soluble drugs. Generally, the release rate is decreased with the decline of drug concentration, and the entire release process is a first-order kinetics process or a fake first-order kinetics process. However, for water-insoluble drugs, it is difficult for drug to release in a dissolution-diffusion mode. If ethyl cellulose is selected as the membrane material, complex solubilization technology has to be used. Thus, the difficulty of the process is increased, and the reproducibility becomes poor. As a result, a large amount of drug will often be residued in the sustained-release pellets or released in an irregular manner.

The application of ethyl cellulose in the semipermeable membrane of osmotic pumps is limited due to its poor permeability. Thus, despite ethyl cellulose could be used as the semipermeable membrane material of osmotic pumps as mentioned in general literatures, ethyl cellulose has not been used in the osmotic pump preparations on the market. Furthermore, it has not been reported in the literatures that ethyl cellulose could be successfully used in the preparations of osmotic pump and thereby achieving good effects.

In addition to aging of the semipermeable membranes mentioned above, the present inventor also found by research that the structures of the existing osmotic pump tablets are also often important reasons causing drug residues, especially for double-compartment or multi-compartment osmotic pump tablets. Taking double-compartment osmotic pump tablets as an example, the double-compartment osmotic pump tablets in the prior art usually belong to symmetric double-compartment osmotic pump tablets with small curvature, i.e., both sides of the tablets are symmetric or substantively symmetric. The angle θ1 and θ2 formed between the outer curved surface (the upper and lower surface in FIG. 1) of the drug-containing layer and the lateral surface are equal or substantially equal and are both small (generally less than 120°), and the ratio $L_1/r$ ($L_1$ is the vertical distance from the central vertex of the outer curved surface (or called "the upper surface") of the drug-containing layer of the tablet core to the plane formed by the intersection line between the upper surface and the lateral surface (FIG. 1), r is the radius of the tablet core (FIG. 1)) is also small (generally less than 0.27) (see FIG. 1). Such a structure results in a corner pocket in the push layer, that is to say, due to the small angle between the outer curved surface of the drug-containing layer and the lateral surface, it is difficult for the drug-containing layer on the edge of the tablet core to be squeezed by the push layer and thus can not move smoothly to the releasing orifices, thereby the push layer is expanded towards the center of the tablet core, so the drug at the edge far away from the central releasing orifices in the drug-containing layer of the tablets can not be easily pushed out. Moreover, the ratio $L_1/r$ ($L_1$ is the vertical distance from the central vertex of the upper surface to the plane formed by the intersection line between the upper surface and the lateral surface, and r is the radius of the tablet core) is smaller, thus the push layer tends to pass through the drug-containing layer and extruded from the releasing orifices. The drug-containing layer residued in the semipermeable membrane cannot be released sustainedly, resulting in a large amount of drug left in the drug-containing layer.

It should be noted that, for the osmotic pump tablets whose outer curved surface of the drug-containing layer belongs to a part of the regular spherical surface, the changes of the above two factors, i.e., (1) the angle θ1 formed between the outer curved surface of the drug-containing layer (the upper surface in FIG. 1) and the lateral surface, and (2) the ratio L1/r (L1 is the vertical distance from the central vertex of the outer curved surface (the upper surface in FIG. 1) to the plane formed by the intersection line between the outer curved surface of the drug-containing layer and the lateral surface (FIG. 1), and r is the radius of the tablet core (FIG. 1)) are consistent, that is to say, the angle θ1 and the ratio L1/r is similarly increased or decreased. However, for the osmotic pump tablets whose outer curved surface of the drug-containing layer belongs to a part of approximate spherical or ellipsoidal surface, the effects of the above two factors (1) and (2) may not be consistent or to the same extent. In other words, factor (1), i.e., the value of angle θ1 has more impact on the drug release at the edge far away from the central release orifice, however, factor (2), i.e., the ratio L1/r has a greater impact on the push layer whether could pass through the drug-containing layer and be squeezed out from the releasing orifices.

SUMMARY OF THE INVENTION

According to the above findings of the present applicant, the osmotic pump controlled release tablets in the prior art have three main defects: (1) the membrane permeability of a semipermeable membrane is reduced due to physical aging caused by ingredient combination with each other; and/or (2) the angle $θ_1$ formed between the outer curved surface of the drug-containing layer and the lateral surface is too small, and (3) the ratio $L_1/r$ ($L_1$ is the vertical distance from the central vertex of the outer curved surface of the drug-containing layer to the plane formed by the intersection line between the outer curved surface of the drug-containing layer and the lateral surface, and r is the radius of the tablet core) is too small. The present invention is made directing to solve one or more of the above defects in the prior art.

On the first aspect, the invention provides an osmotic pump controlled release tablet that can always maintain stable release properties without being affected by storage time. After careful research and selection on the semipermeable membrane material, we surprisingly found that the semipermeable membrane using a combination of ethyl cellulose and povidone as film-forming material can overcome the physical aging. The osmotic pump controlled release tablets using these two components as semipermeable membrane materials can maintain stable release properties within the validity period. Through comparative studies, we surprisingly found that the semipermeable membrane composed of a combination of ethyl cellulose and povidone has almost all the characteristics of the above ideal semipermeable membrane.

Comparative experiments showed that, in the case of the same tablet cores, varying degrees of physical aging are present in the osmotic pump controlled release tablets coated with other commonly used semipermeable membrane material, such as cellulose acetate plus polyethylene glycol, ethyl cellulose plus polyethylene glycol. In contrast, the osmotic pump controlled release tablets using a combination of ethyl cellulose and povidone as a film-forming material of the semipermeable membrane eliminate the phenomenon of physical aging, and can provide a stable release property within the validity period of the pharmaceutical preparation.

A combination of ethyl cellulose and povidone is usually used as film-forming materials of sustained release pellets. Heretofore, it has not been reported that the combination is used in the semipermeable membrane of osmotic pump controlled release tablets. The reason is that the release mechanism of the two dosage forms is different, so the technical problems to be solved are also different. The release mechanism of sustained-release pellets is based on the diffusion theory. Because the particle size of sustained-release pellets is very small, hundreds of pellets are often contained in one dosage unit, so the surface area is very large. The object of membrane-based controlled release is to provide a suitable surface area for release, so that the drug is slowly released, and its release characteristics comply with Higuchi equation. One of the most critical point is that this membrane is not a semipermeable membrane, because not only water can enter, but also drug can release from it. The release mechanism of the osmotic pump controlled release tablets according to the present invention is based on the principle of osmotic pressure. The object thereof is to find an appropriate semipermeable membrane to control water enter into the inside of the membrane, but drug can not be released through the semipermeable membrane and has to be released through the releasing orifices drilled in advance. Its release behavior complies with zero-order release kinetics. Therefore, the two tablets have different release mechanisms and different release characteristics, and solve problems in different ways. Moreover, considering the permeability of ethyl cellulose itself is very low, the conclusion, i.e., the use of a combination of ethyl cellulose and povidone as a film-forming material of the semipermeable membrane of osmotic pump controlled release tablets effectively overcomes the physical aging of the semipermeable membrane, is unexpected.

According to the present invention, in the case that ethyl cellulose and povidone are used as film-forming materials of the semipermeable membrane, when the proportion of povidone in the semipermeable membrane is larger, the membrane permeability is higher, and the release is faster. Moreover, the weight increase after coating is greater, the resistance of membrane diffusion is greater, and the release is slower. For the combination of ethyl cellulose and povidone, if the proportion of povidone is too large, the membrane permeability is too high, and the release is too faster. In contrast, if the proportion of povidone is too small, the membrane permeability is too low, and the release is too slower, alternatively, the membrane permeability becomes too sensitive to the change of the weight increase after coating, so that it is difficult to control the process. Generally, the weight ratio of ethyl cellulose to povidone may be 1:1 to 4:1, preferably 1.5:1 to 3:1. In this case, the membrane permeability is moderate for most drugs. For the weight increase of the semipermeable membrane after coating, if the weight increase is too small, the film is too thin so that the film has a risk of rupture during the release process. If the weight increase is too large, the film is too thick so that the process is lengthy and poor economic. Generally, the weight increase after coating may be 5%-25%, preferably 8%-15%. Both the weight ratio of ethyl cellulose to povidone and the weight increase after coating of the semipermeable membrane can be taken into comprehensive consideration. If the release is too fast, the proportion of povidone can be properly reduced or the weight increase after coating can be properly increased; conversely, if the release is too slow, the proportion of povidone can be properly increased or the weight increase after coating can be properly reduced. Thus, for a specific drug, those skilled in the art, based on the above teachings in combination with drug solubility, can specificly determine the weight ratio of ethyl cellulose to povidone as well as the proper value of the weight increase after coating through simple tests.

Furthermore, the present invention also provides a method for preparing the osmotic pump controlled release tablets methoded above, the method comprises coating the tablet cores with a semipermeable membrane using ethyl cellulose and povidone as film-forming materials, wherein the weight ratio of ethyl cellulose and povidone in the semipermeable membrane is 1:1 to 4:1, preferably 1.5:1 to 3:1.

In addition to ethyl cellulose and povidone as film-forming materials in the semipermeable membrane, other excipients such as a pore-forming agent can also be used in the semipermeable membrane, if necessary.

Furthermore, the present invention also provides the use of a composition comprising ethyl cellulose and povidone for preparing a semipermeable membrane of osmotic pump controlled release tablets. Besides ethyl cellulose and povidone, the composition optionally comprises a solvent, including an organic solvent, such as ethanol, acetone, dichloromethane, and the like, or a certain proportion of an organic solvent-water solution, preferably ethanol and an ethanol-water solution. If necessary, other excipients commonly used such as a pore-forming agent can also be comprised in the semipermeable membrane to improve the performance. During the process of preparing osmotic pump controlled release tablets, the above composition is usually prepared into a coating solution, and coated on the tablet core by the process of coating, and then present in a form of semipermeable membrane in the osmotic pump controlled release tablets after removing the solvent by heat treatment.

Those skilled in the art can select other excipients used in the osmotic pump controlled release tablets in accordance with the known technology regarding the osmotic pump controlled release tablets, and specifically operate in accordance with the known technology regarding the osmotic pump controlled release tablets, such as mixing, granulating, compression, and coating.

The use of ethyl cellulose and povidone as semipermeable film-forming materials is not only applicable to mono-compartment osmotic pump controlled release tablets, but aslo especially suitable for double-compartment or multi-compartment osmotic pump controlled release tablets. For mono-compartment osmotic pump tablets, one or more releasing orifices can be drilled on any surface. For double-compartment or multi-compartment osmotic pump controlled release tablets, one or more releasing orifices are generally drilled on the surface comprising the drug-containing layer, and one releasing orifice is usually drilled.

The semipermeable membrane made of a combination of ethyl cellulose and povidone according to the present invention confer the zero-order drug release characteristics to the osmotic pump controlled release tablets, at the same time, in the respect of storage stability, the physical aging of the semipermeable membrane is avoided. As a result, the release rate remains substantively unchanged after a long-term storage, but even in the extreme conditions (the temperature is 40° C., 60° C., and the relative humidity is RH 75%, 92.5%), the release characteristic remains stable. Because the release keeps basically stable within the validity period, and no excessive feeding is required during the preparation process.

On the second aspect, the present inventor provides a new double-compartment or multi-compartment osmotic pump controlled release tablets. Based on the above defects of drug residues caused by the structure of the existing osmotic pump tablets found by the present inventor, the present inventor made the following improvements:

Firstly, according to the fluid mechanics principle, the curvature of the outer curved surface of the drug-containing layer in the tablet core is increased. Specifically, the curvatures of the two outer curved surfaces of the drug layer and the push layer may be increased (for symmetric double-layer tablets) or only the curvature of the outer curved surface of the drug-containing layer may be increased (for asymmetric double-layer tablets). By increasing the curvature of the outer curved surface of the drug-containing layer, i.e., significantly increasing the angle $\theta_1$ formed between the outer curved surface of the drug-containing layer (i.e., the upper surface in FIG. 1) and the lateral surface (as seen from FIG. 1) to result in a "funnel effect", so that the drug-containing layer on the edge of the tablet core is easier to move along the protrusion of the semipermeable membrane of drug-containing layer to the front of the funnel (the releasing orifice) after being squeezed by the push layer, at the same time, the center of the drug-containing layer is thickened due to the protrusion of the large curvature on the side of the drug-containing layer, which is more helpful to prevent the push layer from passing through the drug-containing layer and directly squeezed out from the releasing orifice (FIG. 2). Our study found that, under the same release conditions, the release rate of the tablet whose angle θ1 was 110° was significantly smaller than that of the tablets whose angle $\theta_1$ was 150°, and the final cumulative release amount of the former was significantly smaller (<90%), and the residue was greater (>10%). With the increasing of angle $\theta_1$, the drug residue decreased continuously. When θ1 is 120°, the drug gan to be less than 10%, and when $\theta_1$ is 130°, the final cumulative release amount was greater than 95%. When the angle θ1 increased to about 150°, the residue was 3.1%. As the angle $\theta_1$ continued to increase to 180°, the change of the release rate was very small, and the drug release had been nearly completed, and the residue was approximately constant. Considering overlarge angle may render the tablet core pressed difficult to leave off molds, the angle $\theta_1$ was preferably 130° to 170°, most preferably about 150°.

As shown in FIG. 1, the horizontal cross section of the tablet core is generally circular, but it also can be elliptical or other shapes, such as polygon, but preferably circular or elliptical. When the horizontal cross section is circular, the angle θ1 of the present invention refers to the angle formed between a tangent line at a point at the intersection between the outer curved surface of the drug-containing layer and the lateral surface with the lateral surface. When the horizontal cross section is elliptical, the angle θ1 refers to the angle formed between a tangent line at the longitudinal cross section along the elliptical long axis of the outer curved surface of the drug-containing layer and the lateral surface. When the horizontal cross section is a regular polygon, the angle θ1 refers to the angle formed between a tangent line at a point at a vertex of the regular polygon and the lateral surface, When the horizontal cross section is other shape, the angle θ1 refers to the angle formed between a tangent line at a point at the longtitude cross section along the gravity center of the tablet core and the furthest vertex and the lateral surface. It should be noted that, the above definition for θ1 also applies to θ2 (i.e. the angle formed between the outer curved surface of the push layer and the lateral surface, as shown in FIG. 1).

In addition, we find that the ratio $L_1/r$ ($L_1$ is the vertical distance from the central vertex of the outer curved surface of the drug-containing layer to the plane formed by the intersection line between the outer curved surface and the lateral surface of the drug-containing layer, r is the radius of the tablet core) (hereinafter referred to as the ratio $L_1/r$) has a significant effect on the drug release residues. As the ratio increases, the thickness of the center of drug-containing layer increases, which can effectively resist the impact of the push layer. As the distance increases, the expansion space of the push layer increases, so that the semipermeable membrane is subject to reduced expansive force produced by the push layer, thereby reducing the possibility of rupture of the semipermeable membrane caused by swelling, and avoiding burst release and non-uniform release. In addition, as the ratio increases, in general, the angle θ1 formed between the outer curved surface of the drug-containing layer and the lateral surface can also be directly increased, which is more helpful to the formation of the "funnel effect", and its advantages are as mentioned above. The ratio $L_1/r$ of the present invention may be 0.27-1.0, preferably 0.36-0.84, more preferably about 0.58. For the radius r of the tablet core, when the horizontal cross section of the drug-containing layer is circular, r refers to the radius of the circle. When the horizontal cross section of the drug-containing layer is elliptic, r refers to the length of the long axle of the ellipse. When the horizontal cross section of the drug-containing layer is regular polygon, r refers to the distance from the vertex of the regular polygon to the symmetric center. When the horizontal cross section of the drug-containing layer is other shape, such as polygon, r refers to the distance from the gravity center of the polygon to the vertex that is furthest away from the gravity center.

In addition, we also find that the outer curved surfaces of the drug-containing layer (as shown in FIG. 1, the upper surface) and the push layer (as shown in FIG. 1, the lower surface) have different curvature (i.e., asymmetric type) can bring about great convenience to the production process. The results show that, in the case that the angles $\theta_1$ formed between the outer curved surface of the drug-containing layer and the lateral surface are equal, the release resistance of the asymmetric type is closer to that of the symmetric type in which the curvatures of the upper and lower surfaces are same and their release rates are roughly comparable. When the osmotic pump tablets belong to the symmetric type, like the symmetric double-layer osmotic pump tablets, the drug-containing layer and the push layer must be distinguished by different colors during the production process, and a laser drilling machine equipped with image recognition function is used to identify the drug-containing layer and the push layer in order to exactly drill orifices on the drug-containing layer. If orifices are drilled on both of the drug-containing layer and the push layer, it can be extruded from an orifice on the push layer after the push layer was expanded, thus affecting the push force and the release rate of the push layer. As a result, the cost for the step of laser drilling is as high as that of the existing symmetric double-compartment osmotic pump tablets. For symmetric osmotic pumps with large curvatures on two sides, since they have a nearly spherical shape, they are very easy to roll and shake when being delivered on the conveyor belt of the drilling machine, so the difficulties of drilling increase. However, for asymmetrical double-compartment osmotic pump tablets, the curvatures of two sides have significant difference, so the drug-containing layer and the push layer can be distinguished from the shape. During the vibration process, the drug-containing layer can face up automatically without an image recognition system, thus, the cost of the laser drilling can be greatly reduced, and the release effect is consistent with symmetric double-layer tablets with large curvatures. Moreover, they keep a steady state when being delivered on the conveyor belt, so the orifices is readily drilled in the middle of the tablets during laser drilling, and it is more helpful for drug to release in a steady manner. Thus, this assymetric curvature type has special benefits.

In addition, the osmotic pump tablets with large curvature of drug-containing layer has according to the present invention is easier to push the drug to be released, compared with the existing osmotic pump tablets with small curvature, the requirements for the push force of the push layer and the deformation of the drug-containing layer are greatly reduced. Existing osmotic pump tablets use high molecular weight of polyoxyethylene (molecular weight generally greater than 5 million) with higher swellability as a push material, and low molecular weight of polyoxyethylene(molecular weight 200, 000) is used in the drug-containing layer to increase the deformation of the drug-containing layer, thereby facilitating the drug to be extruded from the releasing orifices. It is well known that polyoxyethylene is more expensive and has poor stability and harsh storage condition. The storage temperature is −18° C., even so, its validity period is not more than 1.5 years. Under such harsh storage condition, the storage stability of the preparations at room temperature becomes a hidden risk. At room temperature, the molecule chain of high molecular weight of polyoxyethylene will continue to break and become into polyoxyethylene of low molecular weight. As a result, the swellability will be decreased and the push capacity will be decreased, thereby resulting in a great amount of drug residues. This is also one of the reasons causing that the osmotic pump controlled release tablets are not widely used. In addition, in the practical application of polyoxyethylene, we found that its excellent deformation tends to produce a vertical edge difficult to be removed when particles are pressed into the tablet cores. This is because a tiny gap is present between the punch and the punching die, so excellent deformation of polyoxyethylene makes it enter into the gap and form the vertical edge during the pressing process. The vertical edge cannot be removed using ordinary sieve machines since polyoxyethylene has a great toughness. Therefore, in the subsequent coating process, uncontinuous semipermeable membrane is formed, and thus the strength is decreased, and qualified samples cannot be prepared. Thus, the use of polyoxyethylene to prepare osmotic pump controlled release tablets has a high requirement for the accuracy of tablet-pressing machine, which will result in increased production cost. In contrast, the osmotic pump controlled release tablets with specific curvature of the present invention do not have to use polyoxyethylene to increase the push force and the deformation, thus avoid the problems such as the formation of the vertical edge, uncontinuous semipermeable membrane, decreased intensity, moreover, the production cost is greatly reduced.

In conclusion, compared with the osmotic pump controlled release tablets in the prior art, the osmotic pump controlled release tablets with above curvature characteristics have the following significant advantages: (1) rare drug residue; (2) the requirements for the push force of the push layer and the deformation of the drug-containing layer are greatly reduced, so cheaper excipients with better stability can be used; (3) low requirements for the accuracy of tablet-pressing machine; etc.

BRIEF DESCRIPTION OF THE DRAWINGS

The present invention will be better understood by reference to the following figures. Those skilled in the art should appreciate that the following drawings are only given for the purpose of illustration. These figures are not intended to limit the scope of the present invention in any way, wherein.

DETAILED DESCRIPTION OF THE INVENTION

Figure 1:
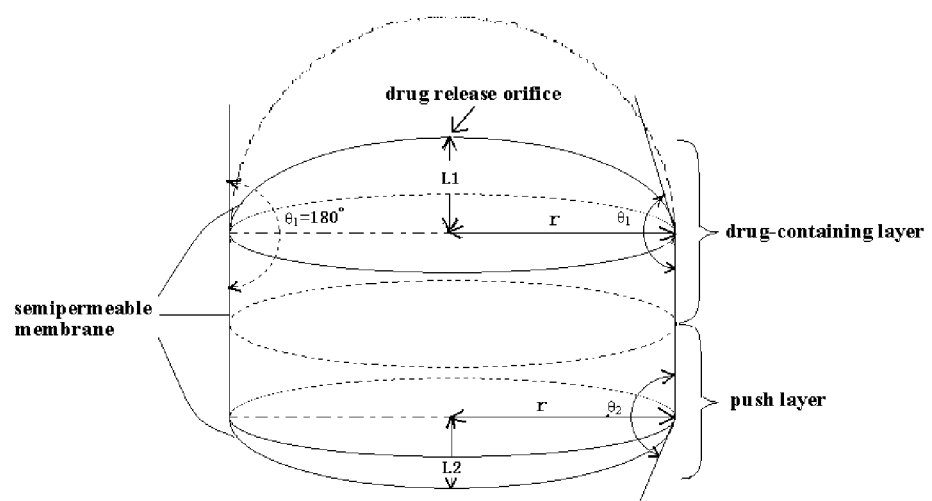
FIG. 1 is a perspective structural view of a double-layer osmotic pump tablet according to the present invention, wherein, the angle formed between the outer curved surface of the drug-containing layer (i.e. the upper surface) and the lateral surface is $\theta_1$; and the angle formed between the outer curved surface of the push layer (i.e. the lower surface) and the lateral surface is $\theta_2$; the vertical distance from the central vertex of the outer curved surface of the drug-containing layer to the plane formed by the intersection line between the outer curved surface of the drug-containing layer and the lateral surface is $L_1$; and the vertical distance from the central vertex of the outer curved surface of the push layer to the plane formed by the intersection line between the outer curved surface of the push layer and the lateral surface is $L_2$. In the figure, when $\theta_1=\theta_2$, the tablet is symmetric double-layer tablet; when $\theta_1>\theta_2$, the tablet is asymmetric double-layer tablet. $\theta_1$ is usually <120° in the prior art.
Figure 2:
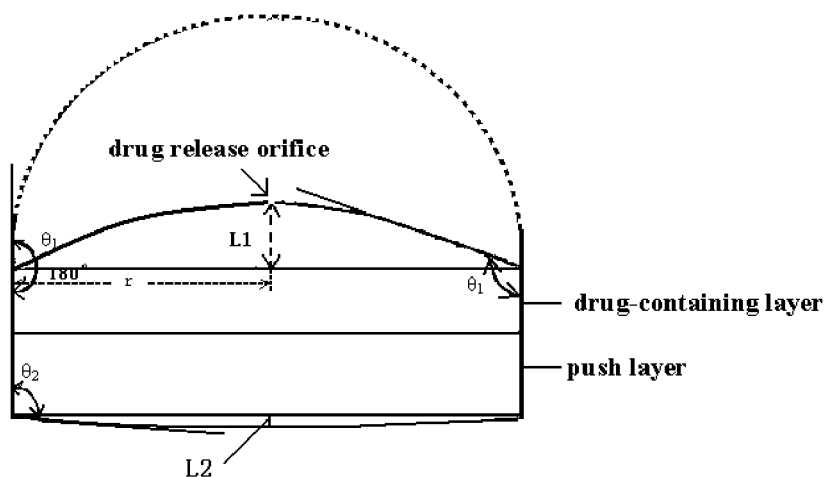
FIG. 2 is a longitudinal sectional view of an asymmetric double-layer osmotic pump according to the present invention, wherein, $\theta_1$, $\theta_2$, L and r are as defined above.

Now, the present invention will be illustrated by various specific embodiments and examples. It should be appreciated that, these examples and embodiments do not intend to limit the scope of the invention. Any improvement and adjustment made by those skilled in the art according to the above relevant teaching combined with known techniques and conventional means in the art will fall within the scope of the present invention.

Firstly, the present invention provides a new type of osmotic pump controlled release preparation, which has one or more advantages as follows: good stability of drug release, small amount of drug residued in the preparation, and low production cost.

In an embodiment of the present invention, an osmotic pump controlled release tablet is provided, wherein ethyl cellulose and povidone are used as film-forming materials for the semipermeable film. In another embodiment, the weight ratio of ethyl cellulose and povidone used as film-forming materials is 1:1 to 4:1, preferably 1.5:1 to 3:1.

The new osmotic pump controlled release tablet according to the present invention comprises structurally a tablet core and a semipermeable film coated on the tablet core. The tablet core is composed of an active pharmaceutical ingredient and optionally one or more penetration-enhancing agents, fillers, pushing agents, cosolvents, lubricants, adhesives or other components. In addition to ethyl cellulose and povidone, the semipermeable membrane may also contain other polymers, plasticizers or pore-forming agents, and releasing orifices are drilled on the semipermeable membrane, and drug is released from the releasing orifices.

The penetration-enhancing agent may be selected from the group consisting of sucrose, sorbitol, mannitol, glucose, lactose, fructose, sodium chloride, potassium chloride, magnesium sulfate, potassium sulfate, sodium sulfate or a combination thereof. The filler may be selected from the group consisting of mannitol, lactose, microcrystalline cellulose, sucrose, sodium chloride, starch, cellulose, dextrin, pre-gelatinized starch, calcium hydrogen phosphate, polyvinyl pyrrolidone, hydroxypropyl methyl cellulose, carboxymethyl cellulose and sodium salt thereof, methyl cellulose, ethyl cellulose or a combination thereof. The pushing agent may be selected from the group consisting of pharmaceutically acceptable expansible materials such as methyl cellulose, hydroxypropyl cellulose, hydroxypropyl methyl cellulose, polyoxyethylene, carbomer, sodium carboxymethyl starch, carboxymethyl cellulose and sodium salt thereof or cross-linked carboxymethyl cellulose sodium or a combination thereof. The cosolvent includes sodium dodecyl sulfate, poloxamer, polyethylene glycol, povidone, polyethylene glycol 15 hydroxystearate, tween 80, hydroxypropyl β-cyclodextrin, polyoxyethylene castor oil, polyoxyethylene hydrogenated castor oil, lecithin or a combination thereof. The lubricant may be selected from the group consisting of magnesium stearate, calcium stearate, zinc stearate, glycerol monostearate, sodium stearyl fumarate, polyoxyethylene monostearate, sucrose monolaurate, sodium lauryl sulfate, magnesium lauryl sulfate, magnesium dodecyl sulfate, talcum powder or a combination thereof. The adhesive may be selected from the group consisting of polyethylene pyrrolidone, hydroxypropyl methyl cellulose, hydroxypropyl cellulose, carboxymethyl cellulose and sodium salt thereof, methyl cellulose, ethyl cellulose or povidone or a combination thereof. The wetting agent may be selected from the group consisting of water, anhydrous ethanol, ethanol-water solution at various concentrations. The plasticizer may be selected from the group consisting of glycerol, propylene glycol, polyethylene glycol, triethyl citrate, dibutyl sebacate, phthalates, polyethylene glycol or a combination thereof. The pore-foaming agent may be selected from the group consisting of hydroxypropyl cellulose, hydroxypropyl methyl cellulose, methyl cellulose, glycerol, propylene glycol, polyethylene glycol, sucrose, mannitol, lactose, sodium chloride or a combination thereof.

The active ingredients useful in the preparations according to the present invention are not limited and may be selected from for example the group consisting of cardiovascular drugs, such as Nifedipine, Felodipine, Isradipine, Nimodipine, Prazosin hydrochloride, Doxazosin mesylate, Diltiazem hydrochloride, Lovastatin, Metoprolol and the like; drugs for treating diabetes, such as Glipizide, and the like; anti-allergy drugs, such as Pseudoephedrine hydrochloride, and the like; anti-asthma drugs, such as Albuterol, and the like; and other drugs suitable for being prepared into sustained-release and controlled release preparations in clinic.

In an embodiment of the present invention, the semipermeable membrane is formed by a coating process. The weight increase of the tablet core after coating relative to that before being coated is 5% to 25%, preferably 8% to 15%.

In another embodiment of the present invention, the tablet core comprises a drug-containing layer and a push layer, wherein:

(1) the angle $\theta_1$ formed between the outer curved surface of the drug-containing and the lateral surface layer is 120° to 180°, and/or (2) the ratio $L_1/r$ ($L_1$ is the vertical distance from the central vertex of the outer curved surface of the drug-containing layer to the plane formed by the intersection line between the outer curved surface of the drug-containing layer and the lateral surface, and r is the radius of the tablet core) is 0.27-1.0.

In a further embodiment of the present invention, the angle $\theta_1$ formed between the outer curved surface of the drug-containing layer and the lateral surface is 130° to 170°, and/or the ratio $L_1/r$ is 0.36-0.84.

In a more preferred embodiment of the invention, the angle $\theta_1$ formed between the outer curved surface of the drug-containing layer and the lateral surface is 150°, and/or the ratio $L_1/r$ ($L_1$ is the vertical distance from the central vertex of the outer curved surface of the drug-containing layer to the plane formed by the intersection line between the outer curved surface of the drug-containing layer and the lateral surface, and r is the radius of the tablet core) is 0.58.

In a still embodiment of the present invention, the angle $\theta_1$ formed between the outer curved surface of the drug-containing layer and the lateral surface is 120° to 180°, and/or the ratio $L_1/r$ ($L_1$ is the vertical distance from the central vertex of the outer curved surface of the drug-containing layer to the plane formed by the intersection line between the outer curved surface of the drug-containing layer and the lateral surface, and r is the radius of the tablet core) is 0.27-1.0; moreover, the angle $\theta_2$ formed between the outer curved surface of the push layer and the lateral surface is 95° to 120°, and/or the ratio $L_2/r$ ($L_2$ is the vertical distance from the central vertex of the outer curved surface of the push layer to the plane formed by the intersection line between the outer curved surface of the push layer and the lateral surface, and r is the radius of the tablet core) is 0.04-0.27. That is to say, an asymmetric double-layer osmotic pump controlled release tablet is formed at this time.

In another specific embodiment of the invention, the angle $\theta_1$ formed between the outer curved surface of the drug-containing layer and the lateral surface is about 150°, and the ratio $L_1/r$ ($L_1$ is the vertical distance from the central vertex of the outer curved surface of the drug-containing layer to the plane formed by the intersection line between the outer curved surface of the drug-containing layer and the lateral surface, and r is the radius of the tablet core) is about 0.58; moreover, the angle $\theta_2$ formed between the outer curved surface of the push layer and the lateral surface is 95° to 120°, and the ratio $L_2/r$ ($L_2$ is the vertical distance from the central vertex of the outer curved surface of the push layer to the plane formed by the intersection line between the outer curved surface of the push layer and the lateral surface, and r is the radius of the tablet core) is 0.04-0.27.

For the double-layer osmotic pump controlled release tablet according to the present invention, the tablet core consists of the drug-containing layer and the push layer, wherein the push layer comprises a push agent, a filler and optionally other excipients.

Accordingly, the present invention also provides a method for preparing the osmotic pump controlled release preparation according to the present invention. The method comprises coating a semipermeable membrane using ethyl cellulose and povidone as film-forming materials on the tablet core. In an embodiment, the weight ratio of ethyl cellulose to povidone is 1:1-4:1. In another embodiment, the weight ratio of ethyl cellulose to povidone 1.5:1 to 3:1. In a further embodiment, the semipermeable membrane is formed by coating process, and the weight increase after coating is 5%-25%, preferably 8%-15%.

In another embodiment of the preparation method, the preparation method includes pressing the drug-containing layer using punches with large curvature surface. In a further embodiment of the preparation method, the preparation method comprises pressing the drug-containing layer using punches with relatively larger curvature surface, while pressing the push layer using punches with relatively smaller curvature surface.

The "large curvature surface" and "small curvature surface" used herein are relative. Those skilled in the art should be able to understand their meaning, and make choices and judgments according to the actual situations. For example, in the case of the present invention, the "large curvature surface" could mean that the angle $\theta_1$ (or $\theta_2$) formed between the outer curved surface of the drug-containing layer (or the push layer) and the lateral surface is equal to or greater than 120°, for example, 130° to 170° or 150°. Similarly, the "small curvature surface" could mean that the angle $\theta_2$ (or $\theta_1$) formed between the outer curved surface of the push layer (or the drug-containing layer) and the lateral surface is less than or equal to 120°, for example 95° to 120°.

In the preparation method of the invention, after coating the semipermeable membrane, the coated tablets can be placed in a dryer and dried by heat treatment for more than 12 h, then one or more releasing orifices with diameter of 0.1-1.5 mm (preferably 0.3 mm-0.8 mm) are drilled by laser on one side of the drug-containing layer of the coated tablets.

In a specific embodiment for preparation of asymmetric double-comparment osmotic pump preparation according to the present invention, the upper punch of the double-layer tablet press is replaced by that with large curvature, and the lower punch is replaced by that with small curvature. The advantages are that the angles from which the tablet cores are pushed out of the middle mold can be reduced, thereby making the tablet cores easy to be pushed out.

Furthermore, in another embodiment of the invention, the invention provides the use of a composition comprising ethyl cellulose and povidone for the preparation of a semipermeable membrane of osmotic pump controlled release tablets.

EXAMPLES

In the following examples, examples 1-3 are the studies made to the effect of the composition of the semipermeable membrane on drug release, and examples 4-5 are the studies made to the effect of the angle θ and the value L/r of the present invention on drug release.

In these examples, examples 1A-1D compared osmotic pump controlled release tablets whose semipermeable membranes were prepared by a combination of ethyl cellulose and povidone according to the present invention with osmotic pump controlled release tablets in the prior art, taking Felodipine as an example. Examples 2A-2B compared osmotic pump controlled release tablets whose semipermeable membranes are prepared by a combination of ethyl cellulose and povidone according to the present invention with osmotic pump controlled release tablets in the prior art, taking Salbutamol sulfate as an example. Examples 3A-3C analyzed the physical aging and stability of the semipermeable membranes and the comparative properties of the membrane materials of the present invention, taking Glipizide as an example. Example 4 compared the release of osmotic pump controlled release tablets in the prior art with osmotic pump controlled release tablets according to the present invention at different angle $\theta_1$ and $L_1/r$, taking Nifedipine as an example. Example 5 compared the release of symmetric and asymmetric double-compartment osmotic pump controlled release tablets of the present invention.

Example 1

Comparative studies on Felodipine Osmotic Pump Controlled Release Tablets

Example 1A

Commercially Available Felodipine Controlled Release Tablets

Manufacturer: Hefei Cubic Pharmaceutical Company Limited
Batch number: 070503
Specification: 5 mg The production date of this batch of commercially available Felodipine controlled release tablets was May, 2007.
Determination of Release:
The release was determined according to the procedure of Felodipine sustained-release tablet in the United States Pharmacopoeia USP30. Current release (2 months from the production date) and the release after being stored in natural conditions for 6 months, 12 months, and 24 months (all of the time points were calculated from the production date). The results were shown in Table 2:

TABLE 2 the release of commercially available Felodipine controlled release tablets at different storage time

| storage time | sampling time (h) | | |
|---|---|---|---|
| | 2 | 6 | 10 |
| limit specified in USP | 10-30% | 42-68% | >75% |
| 2 months | 15.8% | 64.5% | 92.6% |
| 6 months | 13.2% | 60.2% | 83.5% |
| 12 months | 12.8% | 50.9% | 72.1% |
| 24 months | 10.3% | 40.2% | 64.5% |

The experimental results showes that Felodipine controlled release tablets exhibited a good release profile at the initial stage. After being stored for 6 months, the release was reduced to certain extent. As time increased, the membrane aged seriously and the release was reduced more prominently. At the time point of 12 months, Felodipine controlled release tablets was already not qualified.

Example 1B

Felodipine Controlled Release Tablets Using Cellulose Acetate and Polyethylene Glycol (PEG) as Film-Forming Materials 1. Formula
1.1 Formula for the tablet core (1000 tablets) is shown in Table 3.

TABLE 3

Formula for the tablet core of Example 1B (1000 tablets)

| | composition | amount used |
|---|---|---|
| the drug-containing layer | Felodipine | 5 g |
| | lactose | 60 g |
| | sodium chloride | 100 g |
| | sodium dodecyl sulfate | 15 g |
| | sodium carboxymethyl cellulose | 20 g |
| | microcrystalline cellulose | 10 g |
| | 0.2% n-propyl gallate and 10% PVP K30 in 95% ethanol | q.s. |
| | PVP K30 | 5 g |
| | magnesium stearate | 3 g |
| the push layer | hypromellose K4M | 60 g |
| | microcrystalline cellulose | 40 g |
| | sodium chloride | 30 g |
| | iron oxide red | 0.5 g |
| | 8% PVP K30 in 70% ethanol | q.s. |
| | PVP K30 | 5 g |
| | magnesium stearate | 1 g |

1.2 Composition of the coating solution: as shown in Table 4.

TABLE 4

Formula for the coating solution in Example 1B

| composition | amount used |
|---|---|
| cellulose acetate | 12 g |
| polyethylene glycol-6000 | 5 g |
| acetone | 700 ml |
| ethanol | 250 ml |
| water | 50 ml |

2 Preparation process
2.1 Preparation process of the tablet core:
The tablet core is a double-layer tablet, one layer is the drug-containing layer, and another layer is the push layer.
The preparation process is as follows:
The drug-containing layer:
(1) Felodipine was passed through a 100-mesh sieve; sodium dodecyl sulfate was passed through a 100-mesh sieve; sodium chloride was smashed and passed through an 80-mesh sieve;
(2) A formulary amount of Felodipine, sodium chloride, sodium dodecyl sulfate, microcrystalline cellulose, sodium carboxymethyl cellulose were weighed and mixed uniformly in a wet-type granulator;
(3) Damp mass was prepared using a solution of 0.2% n-propyl gallate and 10% PVP K30 in 95% ethanol;

(4) The mixture was granulated by passing through a 24-mesh sieve, dried at 40° C., and then sieved by passing through a 24-mesh sieve;
(5) A formulary amount of magnesium stearate was added and mixed uniformly to obtain the particle of the drug-containing layer.

The push layer:
(1) Sodium chloride was smashed and passed through an 80-mesh sieve;
(2) A formulary amount of hypromellose K4M, microcrystalline cellulose, sodium chloride and iron oxide red were weighed and mixed uniformly in a wet-type granulator;
(3) Damp mass was prepared using a solution of 8% PVP K30 in 70% ethanol;
(4) The mixture was granulated by passing through a 24-mesh sieve, dried at 40° C., and then sieved by passing through a 24-mesh sieve;
(5) A formulary amount of magnesium stearate was added and mixed uniformly to obtain the particle of the push layer.

The above two kinds of particles were pressed into double-layer tablets using 8 mm circular punches.

2.2 Preparation process of the semipermeable membrane

A formulary amount of cellulose acetate was weighed and dissolved in a formulary amount of ethanol to obtain solution 1. The formulary amount of polyethylene glycol-6000 was added to a formulary amount of ethanol and water and stirred to dissolve completely to obtain solution 2. The two solutions were mixed and stirred evenly to obtain the semipermeable membrane.

2.3 Coating (the semipermeable membrane):

The tablet cores were placed in a multi-function coating machine and coated. The spray speed was 3 to 5 ml/min, and the weight increase after coating was 12-13%.

2.4 Heat treatment:

The tablets were subjected to heat treatment at 40° C., 60° C. for 16 h, 24 h and 48 h.

2.5 Drilling by laser:

Orifices with diameter of 0.3-0.7 mm were drilled on one side of the drug-containing layer using a laser drilling machine.

3 Determinaton of the release: the method was as same as Example 1A.

3.1 The release results after heat treatment under different conditions were shown as Table 5 below:

TABLE 5

The release results after heat treatment under different conditions

| heat treatment condition | sampling time (h) | | |
|---|---|---|---|
| | 2 | 6 | 10 |
| 40° C.-16 h | 15.4 | 62.3 | 93.5 |
| 40° C.-24 h | 13.2 | 56.8 | 89.1 |
| 40° C.-48 h | 10.5 | 48.0 | 83.2 |
| 60° C.-16 h | 10.8 | 46.3 | 83.7 |
| 60° C.-24 h | 7.5 | 40.8 | 75.1 |
| 60° C.-48 h | 3.6 | 34.9 | 70.5 |

The above results showed that, for Felodipine controlled release tablets using cellulose acetate and polyethylene glycol (PEG) as film-forming materials, the membrane aged more rapidly and the release was reduced constantly as the heat treatment temperature and the heat treatment time was increased.

3.2 Determinaton of the release after long-term storage: samples subjected to the heat treatment condition of 40° C.-16 h were used. The release was determined at 0 month and 6 months, 12 months and 24 months after being stored under natural conditions. The results were shown in Table 6:

TABLE 6 the release results after long-term storage

| storage time | sampling time (h) | | |
|---|---|---|---|
| | 2 | 6 | 10 |
| 0 month | 15.4 | 62.3 | 93.5 |
| 6 months | 13.8 | 56.3 | 87.2 |
| 12 months | 10.2 | 50.9 | 83.6 |
| 24 months | 7.1 | 40.2 | 71.4 |

The experimental results showed that Felodipine controlled release tablets using cellulose acetate and polyethylene glycol (PEG) as film-forming materials exhibited a good release profile at the initial stage. After being stored for 6 months, the release was reduced at certain extent. As time increased, the membrane aged seriously and the release was reduced more prominently. At the time point of 24 months, Felodipine controlled release tablets was already not qualified.

4 Experiment of weight loss of the membrane

Experimental method: the semipermeable membrane was stripped off the tablet core. After the powder of the tablet core residued on the semipermeable membrane was removed, the semipermeable membrane was weighed and placed in a dissolution cup containing 500 ml of distilled water at 37° C. According to the dissolution determination method I (rotating basket method) in Appendix of Chinese Pharmacopoeia (2005 edition), the rotating speed was 50 rpm, and samples were taken at 1 h and 2 h respectively, dried at 50° C., then was allowed to standed to room temperature and weighed. The weight loss ratio was calculated.

The calculation equation is as follows: the weight loss percentage of the membrane (%)=$W_T/W_0 \times 100\%$ $W^T$: the weight of the membrane after drying at different sampling time points; $W_0$: the initial weight of the membrane.

The results were shown in following Table 7:

TABLE 7 the weight loss results after long-term storage

| storage time | the weight loss percentage of the membrane (%) | |
|---|---|---|
| | 1 h | 2 h |
| 0 month | 28.3 | 28.4 |
| 6 months | 25.4 | 25.4 |
| 12 months | 20.2 | 20.3 |
| 24 months | 17.9 | 18.0 |

The results of the weight loss experiment showed that the binding rate of PEG and cellulose acetate was increased constantly as storage time increases, so that soluble PEG gradually reduced and the permeability of the membrane gradually decreased, and the release rate gradually decreased, suggesting that the aging of the membrane was always accompanied with the semipermeable membrane containing cellulose acetate-PEG.

Example 1C

Felodipine Controlled Release Tablets Using Ethyl Cellulose and Povidone as Film-Forming Materials 1. Formula
1.1 Formula of the tablet core (1000 tablets), as shown in Table 8

TABLE 8

Formula for the tablet core of Example 1C (1000 tablets)

| | composition | amount used |
|---|---|---|
| the drug-containing layer | Felodipine | 5 g |
| | lactose | 60 g |
| | sodium chloride | 100 g |
| | sodium dodecyl sulfate | 15 g |
| | sodium carboxymethyl cellulose | 20 g |
| | microcrystalline cellulose | 10 g |
| | 0.2% n-propyl gallate and 10% PVP K30 in 95% ethanol | q.s. |
| | PVP K30 | 5 g |
| | magnesium stearate | 3 g |
| the push layer | hypromellose K4M | 60 g |
| | microcrystalline cellulose | 40 g |
| | sodium chloride | 30 g |
| | iron oxide red | 0.5 g |
| | 8% PVP K30 in 70% ethanol | q.s. |
| | PVP K30 | 5 g |
| | magnesium stearate | 1 g |

1.2 Composition of the coating solution: as shown in Table 9.

TABLE 9

Formula of the coating solution in Example 1C

| | Formula 1 | Formula 2 | Formula 3 |
|---|---|---|---|
| ethyl cellulose N-100 | 30 g | 30 g | 30 g |
| PVP k30 | 18 g | 16 g | 15 g |
| ethanol | 950 ml | 950 ml | 950 ml |
| water | 50 ml | 50 ml | 50 ml |

2 Preparation process
2.1 Preparation process of the tablet core: The process was as same as Example 1B.
2.2 Preparation process of the semipermeable membrane A formulary amount of ethyl cellulose N-100 and PVP k30 were weighed and added to a formulary amount of ethanol, the mixture was stirred to dissolve completely.
2.3 Coating (the semipermeable membrane):

The tablet cores were placed in a multi-function coating machine and coated. The spray speed was 3 to 5 ml/min. For Formula 1, the weight increase after coating was 16-17%. For Formula 2, the weight increase after coating was 14-15%. The weight increase after coating for Formula 3 was 11-12%.
2.4 Heat treatment:

The tablets were subjected to heat treatment at 40° C., 60° C. for 16 h, 24 h and 48 h.
2.5 Drilling by laser:

Orifices with diameter of 0.3-0.7 mm were drilled on one side of the drug-containing layer using a laser drilling machine.
3 Determinaton of the release: the method was as same as Example 1A.
3.1 The release results after heat treatment at different conditions and the comparasion with commercially available Felodipine sustained-release tablets (produced by AstraZeneca, trade name: plendil®, batch number: 0706023) were seen in Table 10:

TABLE 10

The release results after heat treatment at different conditions

| Formula No. | heat treatment condition | sampling time (h) | | |
|---|---|---|---|---|
| | | 2 | 6 | 10 |
| coating Formula 1 | untreated | 17.2 | 65.3 | 98.6 |
| | 40° C.-16 h | 18.5 | 66.5 | 100.1 |
| | 40° C.-24 h | 17.3 | 65.0 | 99.0 |
| | 40° C.-48 h | 18.9 | 64.9 | 98.9 |
| | 60° C.-16 h | 17.4 | 66.3 | 98.7 |
| | 60° C.-24 h | 18.8 | 65.4 | 99.1 |
| | 60° C.-48 h | 17.1 | 66.0 | 98.5 |
| coating Formula 2 | untreated | 15.4 | 62.1 | 100.2 |
| | 40° C.-16 h | 16.3 | 63.4 | 100.0 |
| | 40° C.-24 h | 15.8 | 62.8 | 98.9 |
| | 40° C.-48 h | 15.3 | 63.3 | 99.1 |
| | 60° C.-16 h | 15.9 | 63.6 | 98.7 |
| | 60° C.-24 h | 15.1 | 62.5 | 99.6 |
| | 60° C.-48 h | 15.5 | 62.0 | 98.3 |
| coating Formula 3 | untreated | 10.2 | 56.1 | 97.9 |
| | 40° C.-16 h | 9.6 | 55.3 | 97.2 |
| | 40° C.-24 h | 10.3 | 56.8 | 98.5 |
| | 40° C.-48 h | 10.6 | 57.9 | 98.1 |
| | 60° C.-16 h | 11.2 | 56.7 | 99.1 |
| | 60° C.-24 h | 10.8 | 56.0 | 98.2 |
| | 60° C.-48 h | 10.9 | 58.1 | 97.1 |
| plendil ® | | 20.1 | 56.7 | 95.4 |

It can be seen from the above table, there is no significant difference between Felodipine osmotic pump controlled release tablets after heat treatment under different conditions, and the release results are comparable with those of the controlled release tablets without heat treatment. In addition, the in vitro release results of Formulas 2 and 3 were very close to those of plendil.

3.2 The release of Formula 3 was determined at 0 month and 6 months, 12 months and 24 months after being stored under natural conditions. The results were shown in Table 11:

TABLE 11 the release results of the samples coated with Formula 3 after long-term storage

| | storage time | sampling time (h) | | |
|---|---|---|---|---|
| | | 2 | 6 | 10 |
| the samples coated with Formula 3 | 0 month | 11.2 | 57.8 | 98.3 |
| | 6 months | 12.3 | 58.2 | 97.8 |
| | 12 months | 11.7 | 60.3 | 96.5 |
| | 24 months | 12.5 | 60.8 | 97.4 |
| plendil ® | 0 month | 20.1 | 56.7 | 95.4 |
| | 6 months | 19.8 | 54.3 | 95.3 |
| | 12 months | 21.2 | 57.4 | 96.9 |
| | 24 months | 23.5 | 58.7 | 97.3 |

It can be seen from the comparison of results of samples after long-term storage at room temperature that, homemade Felodipine controlled release tablets are quite stable during storage, and the in vitro release results are comparable with those of Felodipine sustained release tablets produced by AstraZeneca (plendil®). For the osmotic pump controlled release preparation of Felodipine according to the present invention, it need to be subjected to a relatively long process including allowing water to enter into the tablet core, dissolution and permeation enhancement to make the polymeric material swell and generate a pushing force, its initial release within 2 hours is not as fast as that of sustained release tablets which release drug on surface thereof. However, for such a drug as Felodipine with a half-life exceeding 10 hours, the release difference of 10% within 2 hours will not have a significant effect on overall drug concentration-time curve and pharmacodynamics, moreover, the in vivo environments such as gastrointestinal motility do not have effect on the release of osmotic pump controlled release preparation, thus, the in vivo and in vitro correlation is more excellent.

4 The weight loss of the membrane

Experimental method: the semipermeable membrane was stripped off the tablet core. After the residue powder of the tablet core on the semipermeable membrane was removed, the semipermeable membrane was weighed and placed in a dissolution cup containing 500 ml of distilled water at 37° C. According to the dissolution determination method I (rotating basket method) in Appendix of Chinese Pharmacopoeia (2005 edition), the rotating speed was 50 rpm, and samples were taken at 1 hour and 2 hour respectively, dried at 50° C., then allowed to stand to room temperature and weighed. The weight loss ratio was calculated.

The calculation equation is as follows: the weight loss percentage of the membrane (%)=$W_T/W_0 \times 100\%$
Wherein, $W_T$: the weight of the membrane after drying at different sampling time points; $W_0$: the initial weight of the membrane. The results were shown in the following Table 12:

TABLE 12 the weight loss after long-term storage

| | the weight loss percentage of the membrane (%) | |
|---|---|---|
| storage time | 1 h | 2 h |
| 0 month | 30.2 | 31.5 |
| 6 months | 30.1 | 31.5 |
| 12 months | 30.2 | 31.3 |
| 24 months | 29.8 | 30.9 |

The membrane weight loss experiment showed that the weight loss of the semipermeable membrane made of ethyl cellulose and povidone kept substantively constant as storage time increased, indicating that the stability and the permeability of the membrane remained substantively constant.

TABLE 13

Formula of the tablet core in Example 1D (1000 tablets)

| | composition | amount used |
|---|---|---|
| the drug-containing layer | Felodipine | 5 g |
| | lactose | 60 g |
| | sodium chloride | 100 g |
| | sodium dodecyl sulfate | 15 g |
| | sodium carboxymethyl cellulose | 20 g |
| | microcrystalline cellulose | 10 g |
| | 0.2% n-propyl gallate and 10% PVP K30 in 95% ethanol | q.s. |
| | PVP K30 | 5 g |
| | magnesium stearate | 3 g |
| the push layer | hypromellose K4M | 60 g |
| | microcrystalline cellulose | 40 g |
| | sodium chloride | 30 g |
| | iron oxide red | 0.5 g |
| | 8% PVP K30 in 70% ethanol | q.s. |
| | PVP K30 | 5 g |
| | magnesium stearate | 1 g |

2. Composition of the coating solution: as shown in Table 14.

TABLE 14

Formula of the coating solution in Example 1D

| composition | amount used |
|---|---|
| ethyl cellulose N-100 | 30 g |
| polyethylene glycol-4000 | 15 g |
| ethanol | 800 ml |
| water | 200 ml |

3. Formula combination, operating conditions and determination results

The specific operation and determination method in this example can be referred to Example 1B.

4. Determination of the release after heat treatment at different conditions

The method was as same as that of Example 1A, and the results were shown in Table 15 below.

TABLE 15 the release determination results of Example 1D

| weight increase (%) | heat treatment condition | 0 month sampling time (h) | | | 6 months sampling time (h) | | | 12 months sampling time (h) | | | 24 months sampling time (h) | | |
|---|---|---|---|---|---|---|---|---|---|---|---|---|---|
| | | 2 | 6 | 10 | 2 | 6 | 10 | 2 | 6 | 10 | 2 | 6 | 10 |
| 11.0 | 40° C./14 h | 13.2 | 55.1 | 96.5 | 10.8 | 50.7 | 89.2 | 8.9 | 43.2 | 80.5 | 6.3 | 38.4 | 77.9 |
| | 60° C./14 h | 11.5 | 53.0 | 92.1 | 9.4 | 51.3 | 88.7 | 7.8 | 42.9 | 81.0 | 5.4 | 36.9 | 75.4 |

Example 1D

Felodipine Controlled Release Tablets Using Ethyl Cellulose and Polyethylene Glycol-4000 as Film-Forming Materials 1. Formula of the tablet core, as shown in Table 13.

The release results showed that the release of Felodipine controlled release tablets using ethyl cellulose and polyethylene glycol 4000 as film forming materials of the semipermeable membrane was reduced as storage time increased, indicating that the combination of ethyl cellulose and polyethylene glycol-4000 cannot solve the physical aging of the semipermeable membrane.

Example 2

Comparative Study of Salbutamol Sulfate Osmotic Pump Controlled Release Tablets

Example 2A

Salbutamol Sulfate Controlled Release Tablets Using Cellulose Acetate and Polyethylene Glycol (PEG) as Film-Forming Materials 1. Formula
1.1 Formula of the tablet core (1000 tablets), as shown in Table 16.

TABLE 16

Formula of the tablet core in Example 2A

| composition | amount used |
| --- | --- |
| Salbutamol sulfate | 8 g |
| lactose | 150 g |
| starch | 60 g |
| mannitol | 30 g |
| 6% PVP K30 in 80% ethanol | q.s. |
| magnesium stearate | 2 g |

1.2 Formula of the controlled release coating, as shown in Table 17.

TABLE 17

Formula of the controlled release coating in Example 2A

| composition | amount used |
| --- | --- |
| cellulose acetate | 30 g |
| PEG 4000 | 10 g |
| acetone | 800 ml |
| water | 200 ml |

1.3 Formula of the coating solution, as shown in Table 18.

TABLE 18

Formula of the coating solution in Example 2A

| composition | amount used |
| --- | --- |
| stomach film coating powder | 10.0 g |
| water | 100 ml |

2. Detailed preparation process
2.1 Preparation process of the formula of the tablet core:
(1) Salbutamol sulfate was passed through a 100-mesh sieve;
(2) A formulary amount of Salbutamol sulfate, lactose, starch and mannitol were weighed and mixed uniformly;
(3) Damp mass was prepared with a solution of 6% PVP K30 in 80% ethanol;
(4) The mixture was granulated by passing through a 24-mesh sieve, dried at 40° C., and then sieved by passing through a 24-mesh sieve;
(5) The theoretical tablet weight was calculated;
(6) The mixture was pressed into the tablet cores using shallow concave punches with diameter of 9 mm.
2.2. Preparation process of the coating solution of the semipermeable membrane
A formulary amount of cellulose acetate and PEG 4000 were weighed and dispensed in a solution of acetone/water, then stirred to dissolve completely to obtain the semipermeable membrane.

The weight increase of the semipermeable membrane: 9.0-10.5%

Heat treatment: the tablets were subjected to heat treatment at 60° C. for 16 hours.

Drilling by laser: orifices with diameter of 0.3-0.7 mm were drilled on one side of the tablets prepared using a laser drilling machine.

3. Preparation process of the film coating solution

A formulary amount of film coating powder was weighed, to which water was added, and the mixture was stirred to dissolve completely to obtain the film coating solution.

Film coating: The weight increases of the drilled tablets were 4.0-5.0%.

3 Determinaton of the release:

The release was determined according to the pharmaceutical import standard No. X20000429 of the People's Republic of China, and the specific release determination method is as follows:

According to the release determination method (Chinese Pharmacopoeia, 1995 edition, Part II, Appendix XD, method I), samples were taken, and the devices for dissolution determination method III were applied. 200 ml water was used as the solvent, and the rotating speed was 50 rpm. 3 ml of samples were taken at 3 h, 6 h and 8 h respectively and filtrated. Then, an equal volume of water was immediately added. The continued filtrate was taken and determined according to the chromatographic conditions of the assay. The dissolution amount for each tablet at different times was calculated. The dissolution amount for each tablet at 3 h, 6 h and 8 h should be in the range of 25-50%, 45-85% and over 80% of the labeled amount respectively and should comply with the regulations. The results were shown in Table 19 below.

TABLE 19 the release determination results in Example 2A

| | sampling time (h) | | |
| --- | --- | --- | --- |
| storage time | 3 | 6 | 8 |
| 0 month | 40.4 | 76.7 | 90.7 |
| 6 months | 35.2 | 65.8 | 81.5 |
| 12 months | 25.1 | 55.0 | 71.3 |
| 24 months | 15.0 | 45.1 | 65.2 |

The experimental results showed that Salbutamol sulfate controlled release tablets using cellulose acetate and polyethylene glycol (PEG) as film-forming materials exhibited a good release profile at the initial stage. After being stored for 6 months, the release was reduced at certain extent. As time increased, the membrane aged seriously and the release was reduced more prominently. At the time point of 12 months, the release of Salbutamol sulfate controlled release tablets was already not qualified.

Example 2B

Salbutamol Controlled Release Tablets Using Ethyl Cellulose and Povidone as Film-Forming Materials for Semipermeable Membrane 1. Formula
1.1 Formula of the tablet core: as same as Example 2A.
1.2 Formula of the controlled release coating film: as shown in Table 20.

TABLE 20

Formula of the controlled release coating film in Example 2B

| Formula No. | 1 | 2 | 3 | 4 | 5 | 6 |
|---|---|---|---|---|---|---|
| ethyl cellulose N-100 | 30 g | 30 g | 30 g | 30 g | 30 g | 30 g |
| povidone K30 | 30 g | 20 g | 15 g | 12 g | 10 g | 7.5 g |
| ethanol (ml) | 950 | 950 | 950 | 950 | 950 | 950 |
| water (ml) | 50 | 50 | 50 | 50 | 50 | 50 |

1.3 Formula of the film coating solution: as same as Example 2A.
2. Preparation process, as same as Example 2A, except that the preparation process of the coating solution for the semi-permeable membrane is different. The specific process is as follows:
A formulary amount of ethyl cellulose N-100 and povidone K30 were weighed and dispersed in a solution of anhydrous ethanol/water, and the mixture was stirred to dissolve completely.
The weight increase of coating and the heat treatment condition were as shown in Table 21 below.
3. Determination of the release, as same as Example 2A, and the results were shown in the follwing Table:

TABLE 21 release determination results for samples prepared by different formula and peparation process in Example 2B after long term storage

| the controlled release film No. | weight increase % | heat treatment condition | release data for 0 month (%) | | | release data for 6 months (%) | | | release data for 12 months (%) | | | release data for 24 months (%) | | |
|---|---|---|---|---|---|---|---|---|---|---|---|---|---|---|
| | | | 3 h | 6 h | 8 h | 3 h | 6 h | 8 h | 3 h | 6 h | 8 h | 3 h | 6 h | 8 h |
| 1 | 25.0 | 40° C./16 h | 40.4 | 77.8 | 96.3 | 40.0 | 76.1 | 95.5 | 39.2 | 74.7 | 94.6 | 38.5 | 73.2 | 92.3 |
| | | 60° C./16 h | 38.7 | 72.4 | 97.5 | 39.1 | 74.1 | 93.8 | 38.2 | 73.5 | 91.7 | 38.0 | 72.2 | 89.8 |
| 2 | 17.1 | 40° C./16 h | 38.1 | 77.5 | 95.8 | 38.5 | 78.3 | 93.6 | 37.4 | 78.9 | 93.0 | 36.5 | 76.1 | 92.1 |
| | | 60° C./16 h | 37.2 | 75.4 | 93.2 | 36.2 | 75.0 | 92.8 | 37.2 | 74.7 | 91.9 | 35.2 | 73.5 | 90.8 |
| 3 | 15.2 | 40° C./16 h | 40.8 | 80.3 | 97.3 | 40.3 | 79.1 | 96.5 | 40.2 | 79.7 | 95.6 | 38.5 | 77.2 | 94.3 |
| | | 60° C./16 h | 39.4 | 79.3 | 96.0 | 40.5 | 80.3 | 96.1 | 39.0 | 78.1 | 94.7 | 37.9 | 76.2 | 92.0 |
| 4 | 13.2 | 40° C./16 h | 45.3 | 80.9 | 93.9 | 44.4 | 80.7 | 96.5 | 43.2 | 79.8 | 94.9 | 42.8 | 78.3 | 95.0 |
| | | 60° C./16 h | 45.0 | 81.3 | 95.7 | 43.8 | 80.3 | 95.8 | 41.8 | 78.1 | 94.8 | 40.9 | 79.2 | 93.7 |
| 5 | 9.6 | 40° C./16 h | 40.3 | 71.6 | 89.8 | 40.3 | 71.6 | 89.8 | 40.3 | 71.6 | 89.8 | 40.3 | 71.6 | 89.8 |
| | | 60° C./16 h | 40.9 | 71.3 | 86.0 | 39.7 | 72.5 | 87.8 | 38.9 | 70.3 | 87.2 | 40.5 | 70.1 | 85.0 |
| | 10.5 | 40° C./16 h | 40.4 | 76.7 | 90.7 | 40.9 | 74.4 | 89.0 | 40.0 | 74.8 | 91.2 | 39.4 | 72.6 | 89.0 |
| | | 60° C./16 h | 38.8 | 72.2 | 87.5 | 39.1 | 71.1 | 87.8 | 38.2 | 73.5 | 88.7 | 38.8 | 72.2 | 86.8 |
| 6 | 5.2 | 40° C./16 h | 37.7 | 73.4 | 92.2 | 36.2 | 72.0 | 91.8 | 35.2 | 71.7 | 91.3 | 34.2 | 70.5 | 88.8 |
| | | 60° C./16 h | 36.5 | 73.0 | 91.4 | 35.7 | 70.9 | 90.4 | 34.5 | 70.6 | 88.4 | 33.7 | 67.9 | 86.1 |
| | 8.1 | 40° C./16 h | 35.0 | 71.9 | 90.3 | 34.4 | 70.6 | 88.7 | 33.8 | 68.7 | 87.3 | 32.4 | 66.6 | 84.5 |
| | | 60° C./16 h | 33.2 | 69.7 | 87.8 | 32.4 | 68.4 | 86.5 | 31.6 | 66.5 | 85.1 | 30.7 | 64.3 | 82.4 |

It can be seen from the above table that, the semipermeable membrane consisted of ethyl cellulose and povidone also showed a good thermal stability in mono-compartment osmotic pump controlled release tablets, and had a moderate membrane permeability, so that the requirements for weight increase of coating were reduced during the coating process, and a better production feasibility was achieved. For example, as for coating formula 5, the release difference was very small when the weight increase was in the range of 9.6 to 10.5%, thereby facilitating better quality control during production. The results of samples after long term storage showed that all of Salbutamol osmotic pump controlled release tablets of different coating formula had better stabilities. There was no significant difference in the release data between the samples at 0 day and those after being stored at room temperature for 24 months.

Example 3

Comparative Studies on Glipizide Osmotic Pump Controlled Release Tablets

Example 3A

Commercially Available Glipizide Tablets

Manufacturer: Pfizer Inc., trade name: Glucotrol XL®
Batch number: 85807012
Specification: 5 mg
Determination of the release:
The release was determined according to the pharmaceutical import standard No. X19990222 of the People's Republic of China, and the specific release determination method is as follows:
According to the release determination method (Chinese Pharmacopoeia, 1995 edition, Part II, Appendix XD, method I), samples were taken, and the devices for dissolution determination method II were applied. 900 ml artificial intestinal fluid without pancreatin was used as the solvent, and the rotating speed was 50 rpm. 8 ml of samples were taken at 4 h, 8 h and 16 h respectively and filtrated. Then, 8 ml artificial intestinal fluid without pancreatin was immediately added to the operating containers respectively. The continued filtrates were taken and the absorbance was determined by spectrophotometry method (Chinese Pharmacopoeia, 1995 edition, Part II, Appendix IV A) at a wavelengh of 276 nm respectively. About 50 mg Glipizide reference standard was taken and precisely weighed, then added to a 100 ml flask. 20 ml methanol was added thereto. Glipizide reference standard was dissolved by ultrasonic treatment, diluted with methanol to the mark and shaken uniformly to use as a stock solution. The artificial intestinal fluid without pancreatin was used as the solvent. According to the following dilution method, a certain volume of the stock solution was taken and diluted with an appropriate volume of solvent to a concentration of Glipizide reference solution:

| control solution | dilution method | Glipizide concentration (μg/ml) |
|---|---|---|
| 1# | 1 ml stock solution plus solvent to 200 ml | 2.5 |
| 2# | 1 ml stock solution plus solvent to 100 ml | 5.0 |
| 3# | 3 ml stock solution plus solvent to 100 ml | 15.0 |
| 4# | 25 ml 1# stock solution plus solvent to 50 ml | 1.25 |
| 5# | 25 ml 3# stock solution plus the solvent to 50 ml | 7.5 |
| 6# | 25 ml 4# stock solution plus the solvent to 50 ml | 0.625 |

6#, 4#, 1#, 2# and 5# control solutions were taken respectively. The absorbances were determined by the same method, and a standard curve was plotted. The release amount at different times for each tablet was caclulated according to the standard curve. The release amount for each tablet at 4 h, 8 h and 16 h should be correspondingly no more than 30%, 30-70% and 85% of the labeled amount respectively and should comply with the regulations.

The releases were determined at 0 month and 6 months, 12 months and 24 months after storage under natural conditions, and the results were shown in the following Table 22:

TABLE 22

The release of commercially available Glipizide controlled release tablets Glucotrol XL ® at different storage time

| | sampling time (h) | | | |
|---|---|---|---|---|
| | 4 | 8 | 12 | 16 |
| | | standard limit | | |
| storage time | <30 | 30-70 | | >85 |
| 0 month | 15.8 | 55.4 | 87.9 | 108.7 |
| 6 months | 13.2 | 51.2 | 83.2 | 98.5 |
| 12 months | 10.8 | 45.7 | 78.8 | 93.5 |
| 24 months | 7.0 | 40.1 | 72.4 | 90.2 |

The experimental results showed that commercially available Glipizide controlled release tablets Glucotrol XL® exhibited a good release profile at the initial stage. After being stored for 6 months, the release was reduced. As time increased, the membrane aged seriously and the release was reduced constantly. Although the release was still within the allowable limits, the drug residue increased.

The factors influencing the stability were examined under more harsh conditions using commercially available Glucotrol XL®, and the results were shown in Table 23.

TABLE 23 the results of the factors influencing the stability of commercially available Glipizide controlled release tablets Glucotrol XL ®

| | sampling time (h) | | | |
|---|---|---|---|---|
| | 4 | 8 | 12 | 16 |
| | | standard limit | | |
| storage time | <30 | 30-70 | | >85 |
| 0 day | 14.1 | 48.5 | 87.2 | 108.6 |
| 40° C.-48 h | 13.2 | 47.2 | 84.5 | 107.1 |
| 40° C.-5 days | 13.8 | 49.2 | 91.6 | 104.6 |
| 40° C.-10 days | 17.4 | 54.6 | 87.9 | 107.4 |
| 60° C.-24 h | 11.7 | 37.2 | 71.1 | 98.8 |

TABLE 23-continued the results of the factors influencing the stability of commercially available Glipizide controlled release tablets Glucotrol XL ®

| | sampling time (h) | | | |
|---|---|---|---|---|
| | 4 | 8 | 12 | 16 |
| | | standard limit | | |
| storage time | <30 | 30-70 | | >85 |
| 60° C.-48 h | 10.9 | 35.4 | 62.8 | 81.7 |
| 60° C.-5 days | 9.9 | 41.8 | 54.5 | 68.1 |
| 60° C.-10 days | 4.2 | 20.7 | 40.3 | 58.9 |
| RH 75%-5 days | 10.2 | 49.0 | 86.4 | 106.9 |
| RH 75%-10 days | 9.3 | 47.2 | 85.1 | 105.4 |
| RH 92.5%-5 days | 9.8 | 48.3 | 86.4 | 106.1 |
| RH 92.5%-10 days | 8.1 | 47.4 | 85.9 | 109.3 |

The results of the above factors influencing the stability showed that the tablets had less stability under conditions of 60° C., due to the use of PEG 6000 as a plasticizer (see Physican's Desk Reference, Glucotrol XL®). DSC thermograms showed that it was present in a liquefied state at 60° C. which is higher than the melting point of PEG 6000. Thus, the integration of PEG 6000 with cellulose acetate was accelerated, resulting in excessive aging.

The release residue was produced for Glucotrol XL® due to the presence of membrane aging. In order to ensure the release meet the standard within a validity period of two years, the feeding was increased during the preparation. The drug content is 105%-115% as stipulated in the standards, however, the measured drug content was 114.3%.

Example 3B

Glipizide Controlled Release Tablets Using Cellulose Acetate and Poly Ethylene Glycol (PEG) as Film-Forming Materials 1. Formula 1.1 Formula of the tablet core (1000 tablets), as shown in Table 24

TABLE 24

Formula of the tablet core in Example 3B

| | composition | amount used |
|---|---|---|
| the drug-containing layer | Glipizide | 10 g |
| | lactose | 35 g |
| | sodium chloride | 25 g |
| | sodium dodecyl sulfate | 10 g |
| | sodium carboxymethyl cellulose | 20 g |
| | PVP k30 | 10 g |
| | 10% PVP k30 in 85% ethanol | q.s. |
| | magnesium stearate | 2 g |
| the push layer | hypromellose K4M | 40 g |
| | microcrystalline cellulose | 50 g |
| | sodium chloride | 30 g |
| | PVP k30 | 10 |
| | iron oxide red | 0.5 g |
| | 10% PVP K30 in 85% ethanol | q.s. |
| | magnesium stearate | 1 g |

1.2 composition of the coating solution: as shown in Table 25.

TABLE 25

Formula of the coating solution in Example 3B

| composition | amount used |
|---|---|
| cellulose acetate | 12 g |
| polyethylene glycol 4000 | 4 g |
| diethyl phthalate | 3 g |
| acetone | 150 ml |
| ethanol | 30 ml |
| water | 20 ml |

2 Preparation process 2.1 Preparation process of the tablet core:
(1) Glipizide was passed through a 100-mesh sieve;
(2) A formulary amount of lactose, sodium chloride, sodium dodecyl sulfate, sodium carboxymethyl cellulose and PVP K30 according to the drug-containing layer were weighed and mixed uniformly;
(3) Damp mass was prepared by a solution of 10% PVP k30 in 85% ethanol;
(4) The mixture was granulated by passing through a 24-mesh sieve, dried at 40° C., and then sieved by passing through a 24-mesh sieve. A formulary amount of magnesium stearate was added to obtain the particles of the drug-containing layer for use;
(5) A formulary amount of hypromellose K4M, microcrystalline cellulose, sodium chloride, PVP k30 and iron oxide red according to the push layer were weighed and mixed uniformly;
(6) Damp mass was prepared by a solution of 10% PVP k30 in 85% ethanol;
(7) The mixture was granulated by passing through a 24-mesh sieve, dried at 40° C., and then sieved by passing through a 24-mesh sieve. A formulary amount of magnesium stearate was added to obtain the particles of the push layer for use;
(8) The theoretical tablet weight was calculated;
(9) Double-layer tablet core were pressed using circular punches with diameter of 9 mm on a double-layer tablet-pressing machine.

2.2 Preparation process of the coating solution for the semipermeable membrane:
A formulary amount of cellulose acetate and PEG 4000 were dispersed in a solution of acetone/ethanol/water and stirred to dissolve completely to obtain the coating solution.

2.3 The weight increase of the semipermeable membrane: 16.8%, 18.7% and 20.2%.

2.4 Heat treatment: the tablets were subjected to heat treatment at 40° C. for 16 hours.

2.5 Drilling by laser: orifices with diameter of 0.5 mm were drilled on one side of the drug-containing layer using a laser drilling machine.

3. Determinaton of the release: the method was as same as Example 3A. The results were shown in Tables 26-29 below.

TABLE 26 the release determination results at 0 day of Example 3B

| weight increase (%) | the release results at 0 day (%) | | | |
|---|---|---|---|---|
| | 4 h | 8 h | 12 h | 16 h |
| 16.8 | 28.1 | 62.0 | 87.4 | 96.9 |
| 18.7 | 26.3 | 57.9 | 85.6 | 95.1 |
| 20.2 | 20.0 | 53.1 | 82.9 | 93.1 |

TABLE 27 the release determination results at 6 months of Example 3B

| weight increase (%) | the release results at 6 months (%) | | | |
|---|---|---|---|---|
| | 4 h | 8 h | 12 h | 16 h |
| 16.8 | 17.3 | 55.3 | 85.4 | 93.8 |
| 18.7 | 15.1 | 50.9 | 80.6 | 92.6 |
| 20.2 | 13.4 | 48.9 | 77.3 | 90.1 |

TABLE 28 the release determination results at 12 months of Example 3B

| weight increase (%) | the release results at 12 months (%) | | | |
|---|---|---|---|---|
| | 4 h | 8 h | 12 h | 16 h |
| 16.8 | 15.2 | 51.6 | 82.1 | 90.5 |
| 18.7 | 13.2 | 46.0 | 75.1 | 89.1 |
| 20.2 | 10.8 | 40.5 | 73.2 | 85.3 |

TABLE 29 the release determination results at 24 months of Example 3B

| weight increase (%) | the release results at 24 months (%) | | | |
|---|---|---|---|---|
| | 4 h | 8 h | 12 h | 16 h |
| 16.8 | 11.5 | 40.8 | 73.2 | 85.9 |
| 18.7 | 10.2 | 38.4 | 70.5 | 83.0 |
| 20.2 | 7.9 | 33.5 | 68.2 | 79.8 |

The experimental results showed that Glipizide controlled release tablets using cellulose acetate and poly ethylene glycol (PEG) as film-forming materials exhibited a good release profile at the initial stage. After being stored for 6 months, the release was reduced at certain extent. As time increased, the membrane aged seriously and the release was reduced more prominently. The releases of formula with 18.7% and 20.2% weight increase of coating were already not qualified at the time point of 24 months. The results were consisitent with those of commercially available products after long-term storage (the releases were reduced by about 20% after 24 months), indicating that the combination of cellulose acetate and polyethylene glycol resulted in the problem of aging, thus the stabilities of the samples had potential risks.

Example 3C

Glipizide Controlled Release Tablets Using Ethyl Cellulose and Povidone as Film-Forming Materials 1. Formula Formula of the tablet core: as same as Example 3B Formula of the coating solution: the formula and the weight increase of coating were shown in Table 30 below:

TABLE 30 the formula of the coating solution in Example 3C and the weight increase of coating

| composition | Formula 1 | Formula 2 | Formula 3 |
|---|---|---|---|
| ethyl cellulose N-100 | 30 | 30 | 30 |
| PVP k30 | 14 | 16 | 18 |
| ethanol | 950 ml | 950 ml | 950 ml |
| water | 50 ml | 50 ml | 50 ml |
| weight increase % | 10.9 | 13.3 | 16.7 |
|  | 13.0 | 15.1 | 18.5 |

2 Preparation process

Preparation process of the coating solution for the semipermeable membrane was as follows:

A formulary amount of ethyl cellulose and PVP k30 were weighed, dispersed in a solution of ethanol-water, and then stirred to dissolve completely to obtain the coating solution.

Heat treatment conditions: the tablets were subjected to heat treatment at 40° C. for 14 hours and at 60V for 14 hours.

The other parts of the preparation process were as same as Example 3B, wherein the weight increases were shown in Table 30.

3 Determinaton of the release: The results were shown in Tables 31-34:

TABLE 31 the release determination results of Example 3C at 0 day

| Formula No. | weight increase | heat treatment condition | \multicolumn{4}{c}{the release results at 0 day (%)} | | | |
|---|---|---|---|---|---|---|
|  |  |  | 4 h | 8 h | 12 h | 16 h |
| 1 | 10.9% | 40° C./14 h | 23.1 | 60.2 | 90.0 | 101.2 |
|  |  | 60° C./14 h | 22.9 | 58.6 | 87.8 | 100.5 |
|  | 13.0% | 40° C./14 h | 18.0 | 49.6 | 79.3 | 98.6 |
|  |  | 60° C./14 h | 17.8 | 48.3 | 79.0 | 99.4 |
| 2 | 13.3% | 40° C./14 h | 18.9 | 53.2 | 85.4 | 99.6 |
|  |  | 60° C./14 h | 17.3 | 53.0 | 84.8 | 99.1 |
|  | 15.1% | 40° C./14 h | 14.4 | 48.2 | 73.9 | 98.3 |
|  |  | 60° C./14 h | 13.2 | 44.4 | 71.9 | 98.0 |
| 3 | 16.7% | 40° C./14 h | 20.3 | 51.8 | 83.7 | 97.4 |
|  |  | 60° C./14 h | 19.8 | 52.1 | 84.0 | 98.5 |
|  | 18.5% | 40° C./14 h | 13.9 | 44.1 | 73.0 | 97.7 |
|  |  | 60° C./14 h | 14.7 | 43.8 | 70.4 | 96.2 |

TABLE 32 the release determination results of Example 3C at 6 months

| Formula No. | weight increase | heat treatment condition | the release results at 6 months (%) | | | |
|---|---|---|---|---|---|---|
|  |  |  | 4 h | 8 h | 12 h | 16 h |
| 1 | 10.9% | 40° C./14 h | 22.8 | 61.5 | 90.2 | 100.8 |
|  |  | 60° C./14 h | 20.9 | 57.0 | 88.4 | 99.3 |
|  | 13.0% | 40° C./14 h | 18.2 | 50.5 | 79.6 | 97.0 |
|  |  | 60° C./14 h | 17.1 | 47.3 | 79.4 | 100.2 |
| 2 | 13.3% | 40° C./14 h | 17.0 | 51.7 | 83.2 | 98.3 |
|  |  | 60° C./14 h | 17.4 | 52.8 | 83.1 | 97.5 |
|  | 15.1% | 40° C./14 h | 12.5 | 47.6 | 74.5 | 99.6 |
|  |  | 60° C./14 h | 11.0 | 43.5 | 75.7 | 98.2 |
| 3 | 16.7% | 40° C./14 h | 18.1 | 50.2 | 82.4 | 98.2 |
|  |  | 60° C./14 h | 18.4 | 51.3 | 83.5 | 99.3 |
|  | 18.5% | 40° C./14 h | 12.6 | 42.7 | 72.4 | 97.0 |
|  |  | 60° C./14 h | 13.3 | 43.6 | 71.9 | 96.7 |

TABLE 33 the release determination results of Example 3C at 12 months

| Formula No. | weight increase | heat treatment condition | the release results at 12 months (%) | | | |
|---|---|---|---|---|---|---|
|  |  |  | 4 h | 8 h | 12 h | 16 h |
| 1 | 10.9% | 40° C./14 h | 20.7 | 57.1 | 86.5 | 99.3 |
|  |  | 60° C./14 h | 19.2 | 53.8 | 84.7 | 96.5 |
|  | 13.0% | 40° C./14 h | 17.4 | 48.3 | 80.2 | 99.3 |
|  |  | 60° C./14 h | 16.8 | 45.2 | 77.8 | 98.0 |
| 2 | 13.3% | 40° C./14 h | 15.5 | 45.3 | 80.2 | 95.9 |
|  |  | 60° C./14 h | 16.3 | 52.7 | 82.8 | 98.4 |
|  | 15.1% | 40° C./14 h | 12.8 | 46.9 | 76.8 | 96.4 |
|  |  | 60° C./14 h | 13.2 | 44.4 | 77.9 | 98.0 |
| 3 | 16.7% | 40° C./14 h | 16.3 | 48.6 | 79.3 | 99.0 |
|  |  | 60° C./14 h | 17.5 | 50.1 | 82.9 | 96.7 |
|  | 18.5% | 40° C./14 h | 10.9 | 43.2 | 74.8 | 96.0 |
|  |  | 60° C./14 h | 13.3 | 43.6 | 72.3 | 96.9 |

TABLE 34 the release determination results of Example 3C at 24 months

| Formula No. | weight increase | heat treatment condition | the release results at 24 months (%) | | | |
|---|---|---|---|---|---|---|
|  |  |  | 4 h | 8 h | 12 h | 16 h |
| 1 | 10.9% | 40° C./14 h | 18.8 | 55.3 | 84.7 | 98.6 |
|  |  | 60° C./14 h | 17.9 | 52.4 | 83.1 | 97.0 |
|  | 13.0% | 40° C./14 h | 16.0 | 46.2 | 78.3 | 96.5 |
|  |  | 60° C./14 h | 14.7 | 43.0 | 74.8 | 95.3 |
| 2 | 13.3% | 40° C./14 h | 14.7 | 42.0 | 75.9 | 96.8 |
|  |  | 60° C./14 h | 13.1 | 43.5 | 76.4 | 97.8 |
|  | 15.1% | 40° C./14 h | 10.5 | 47.2 | 75.3 | 99.1 |
|  |  | 60° C./14 h | 9.7 | 43.5 | 74.8 | 96.7 |
| 3 | 16.7% | 40° C./14 h | 15.4 | 46.9 | 77.1 | 98.2 |
|  |  | 60° C./14 h | 14.5 | 42.7 | 73.2 | 98.0 |
|  | 18.5% | 40° C./14 h | 11.0 | 45.1 | 76.3 | 96.7 |
|  |  | 60° C./14 h | 12.8 | 44.7 | 74.5 | 94.8 |

It can be seen from above tables that, samples with different weight increase of coating of each formula under different heat treatment conditions had good stabilities after long-term storage. The release could be adjusted by the following two modes: (1) changing the weight ratio of ethyl cellulose to povidone to control the membrane permeability; and (2) changing the weight increase of coating. Because the membrane did not age during storage, different membranes with different weight increase of coating showed good stabilities. In addition, because the membrane did not age during storage, the release residue was very small, and thus no excessive feeding was required.

It shoud be noted that, except commercially available Glipizide sustained-release tablets (Glucotrol XL®), the most common shapes in the prior art were used for the tablets in Examples 1-3, i.e., the angle θ1 and the ratio L1/r for the drug-containing layer as well as the angle θ2 and the ratio L2/r for the push layer were all about 110° and 0.18. In contrast, the angle and the ratio of commercially available Glipizide sustained-release tablets (Glucotrol XL®) as determined were a little greater, i.e., about 115-119° and 0.22-0.26.

Example 4

Comparative Studies on Nifedipine Osmotic Pump Controlled Release Tablets

Example 4A

The Release Data of Commercially Available Nifedipine Osmotic Pump Controlled Release Tablets Trade name: Adalat
Manufacturer: Bayer Healthcare Company Limited
Batch number: 110300
Specification: 30 mg
Production date: October 25, 2006
Shape: symmetric, the determined values of the angle $\theta_1$ and the ratio $L_1k$ for the drug-containing layer as well as the angle $\theta_2$ and the ratio $L_2/r$ for the push layer were both about 115-119° and 0.22-0.26.

1. Influence factors trial
Experimental Method:
The samples were placed under 40° C., 60° C., RH75%, RH92.5% and light (45001×) respectively. Samples were taken and determined at day 5 and day 10, respectively.
Determination method and standard for release:
The releases were determined according to the pharceumatical import standard No. X20010169 for Nifedipine controlled release tablets (Adalat). The specific method was as follows: according to the dissolution determination method (Chinese Pharmacopoeia (2000 edition), Part II, Appendix XC, method II), under dark condition, the tablets were taken and placed in metal baskets. The solvent was 900 ml 1% sodium dodecyl sulfate in a phosphate-citric acid buffer solution (pH=6.8). The rotating speed was 100 rpm. An appropriate amount of filtrates were taken at 4, 12 and 24 hours respectively. In addition, about 18 mg of Nifedipine was taken as a control, and precisely weighed in a 50 ml brown volumetric flask. Nifedipine was dissolved and diluted to the mark by adding a mixed solution of acetonitrile-methanol (50:50). 5 ml solution was precisely taken and placed in a 25 ml brown volumetric flask. A mixed solution of acetonitrile-methanol-water (25:25:50) was added and diluted to the mark, then shaken uniformly.

HPLC conditions: octadecylsilane chemically bonded silica was used as a filler. A guard column was equipped. A mixture of acetonitrile-methanol-water (20:30:50) was used as the mobile phase. The detection wavelength was 265 nm, and the theoretical plate number was no less than 5000, calculated based on the peak of Nifedipine.

According to the above HPLC conditions, 10 μl solution was taken and injected into the liquid chromatograph respectively to determine the peak area. The content of Nifedipine at different time was calculated according to external standard method. The dissolution amount for each tablet at 4, 12 and 24 hours should be in the range of 5% to 17%, 43% to 80% and more than 85% of the labelled amount respectively. The results were shown in Table 35:

TABLE 35 the results of the influence factors of Adalat

| Factors | content (%) | 4 h | 6 h | 12 h | 24 h |
|---|---|---|---|---|---|
| 0 day | 114.5 | 9.9 | 26.1 | 52.8 | 97.8 |
| 40° C., 10 days | 113.9 | 7.3 | 24.5 | 48.9 | 96.0 |
| 60° C., 10 days | 114.0 | 11.2 | 23.2 | 45.0 | 75.5 |
| Under light, 10 days | 114.4 | 10.1 | 24.4 | 50.3 | 95.4 |
| RH75%, 10 days | 113.8 | 10.5 | 29.6 | 57.3 | 97.9 |
| RH92.5%, 10 days | 114.0 | 15.3 | 30.0 | 60.9 | 98.4 |

2. Long-term storage at room temperature: The tablets were stored at room temperature. The release data were determined at 3 months, 6 months, 12 months and 24 months after production date. The release determination method and standard were described as above. The results were shown in Table 36.

TABLE 36

The release of Adalat at different storage time

| storage time | sampling time (h) and release (%) | | | |
|---|---|---|---|---|
| | 4 h | 6 h | 12 h | 24 h |
| 3 months | 9.9 | 26.1 | 52.8 | 97.8 |
| 6 months | 8.7 | 24.8 | 50.2 | 95.4 |
| 12 months | 9.0 | 23.1 | 48.9 | 92.0 |
| 24 months | 7.5 | 22.6 | 45.9 | 88.3 |

The experimental results showed that commercially available Nifedipine osmotic pump controlled release tablets exhibited a good release profile at the initial stage. After being stored for 6 months at room temperature, the release was reduced at certain extent. As time increased, the membrane aged seriously and the release was reduced more prominently.

In addition, the experimental data of the above two experiments also showed that, commercially available Nifedipine osmotic pump controlled release tablets Adalat had obvious drug residue, so excessive feeding was necessary, and the content at the production date reached more than 110%, but only 95-100% could be generally released. After long-term storage, the release was reduced more obviously.

Example 4B

Comparative Studies on the Release of Nifedipine Double-Compartment Osmotic Pump Controlled Release Tablets with Different Angle $\theta_1$ and $L_1/r$ value 1. Formula
1.1 Formula of the tablet core (1000 tablets)

The Drug-Containing Layer of the Tablet Core

| composition | amount used (g) |
|---|---|
| Nifedipine | 30 |
| sodium chloride | 40 |
| lactose | 30 |
| sodium dodecyl sulfate | 20 |
| sodium carboxymethyl cellulose | 30 |
| PVP K30 | 10 |
| 10% PVP K30 in 70% ethanol | q.s. |
| magnesium stearate | 2 |

The Push Layer of the Tablet Core

| composition | amount used (g) |
|---|---|
| hypromellose K4M | 50 |
| microcrystalline cellulose | 20 |
| sodium chloride | 30 |
| iron oxide red | 0.5 |
| PVPK 30 | 10 |
| 10% PVP K30 in 70% ethanol | q.s. |
| magnesium stearate | 0.5 |

1.2 composition of the coating solution: as shown in Table 37.

TABLE 37

Formula of the coating solution in Example 4

| composition | amount used |
|---|---|
| cellulose acetate | 12 g |
| polyethylene glycol 6000 | 4 g |
| diethyl phthalate | 3 g |
| acetone | 150 ml |
| ethanol | 30 ml |
| water | 20 ml |

2 Preparation process 2.1 Preparation process of the tablet core:

(1) Nifedipine was passed through a 100-mesh sieve;

(2) A formulary amount of lactose, sodium chloride, sodium dodecyl sulfate, sodium carboxymethyl cellulose and PVP K30 according to the drug-containing layer were weighed and mixed uniformly;

(3) Damp mass was prepared with a solution of 10% PVP K30 in 70% ethanol;

(4) The mixture was granulated by passing through a 24-mesh sieve, dried at 40° C., and then sieved by passing through a 24-mesh sieve. A formulary amount of magnesium stearate was added to obtain the particles of the drug-containing layer for use;

(5) A formulary amount of hypromellose K4M, microcrystalline cellulose, sodium chloride, PVP k30 and iron oxide red according to the push layer were weighed and mixed uniformly;

(6) Damp mass was prepared with a solution of 10% PVP k30 in 70% ethanol;

(7) The mixture was granulated by passing through a 24-mesh sieve, dried at 40° C., and then sieved by passing through a 24-mesh sieve. A formulary amount of magnesium stearate was added to obtain the particles of the push layer for use;

(8) The theoretical tablet weight was calculated; Nifedipine was passed through a 100-mesh sieve;

(9) The theoretical tablet weight was calculated;

(10) Double-layer tablets were pressed on a double-layer tablet-pressing machine, wherein the push layer was pressed using shallow circular punches with diameter of 8 mm, and the drug-containing layer was pressed using deep circular punches with diameter of 8 mm and different angles. Asymmetric tablet cores were prepared respectively, wherein, the angle $\theta_1$ formed between the outer curved surface of the drug-containing layer and the lateral surface and the ratio $L_1$ were 110° (0.18), 120° (0.27), 130° (0.36), 140° (0.47), 150° (0.58), 160° (0.70), 170° (0.84), and 180° (1.0) (Note: the values in the parentheses are the ratio $L_1/r$)respectively, and the angle $\theta_2$ formed between the outer curved surface of the push layer and the lateral surface and the ratio $L_2/r$ were 110° (0.18).

2.2 Preparation process of the coating solution for the semipermeable membrane:

A formulary amount of cellulose acetate and PEG 6000 were weighed, dispensed in a solution of acetone/ethanol/water, and then stirred to dissolve completely to obtain the coating solution.

2.3 Weight increase of coating of the semipermeable membrane: 18.4-18.6%.

2.4 Heat treatment: the tablets were subjected to heat treatment at 40° C. for 16 hours.

2.5 Drilling by laser:

Orifices with diameter of 0.5 mm were drilled on one side of the drug-containing layer using a laser drilling machine.

3 Determinaton of the release:

The method was as same as Example 4A. The results were shown in Table 38.

TABLE 38 the release results of Example 4B

| | | accumulative release at different angle $\theta_1$ and ratio $L_1/r$ (%) | | | | | | | |
|---|---|---|---|---|---|---|---|---|---|
| | | 110° (0.18) | 120° (0.27) | 130° (0.36) | 140° (0.47) | 150° (0.58) | 160° (0.70) | 170° (0.84) | 180° (1.0) |
| eeight increase | | 18.4% | 18.5% | 18.4% | 18.5% | 18.6% | 18.5% | 18.4% | 18.5% |
| sampling time | 4 h | 8.3 | 8.5 | 9.3 | 11.3 | 11.1 | 10.9 | 12.2 | 11.9 |
| | 6 h | 22.9 | 23.5 | 26.9 | 28.1 | 28.7 | 27.6 | 29.2 | 28.2 |
| | 12 h | 58.8 | 60.2 | 64.7 | 66.9 | 68.3 | 67.0 | 68.2 | 70.4 |
| | 24 h | 92.3 | 93.5 | 98.0 | 98.1 | 97.7 | 97.7 | 97.8 | 98.3 |
| content (%) | | 102.6 | 102.3 | 102.4 | 101.7 | 100.8 | 100.6 | 101.6 | 101.4 |
| residue (%) | | 10.3 | 8.8 | 4.4 | 3.6 | 3.1 | 2.9 | 2.8 | 3.1 |

It could be seen from the results that, under the same release conditions, the release rates of the tablets whose angle θ1 and ratio L1/r were 110° (0.18) were significantly slower than those of the tablets whose angle θ1 and ratio L1/r were 150° (0.58). Moreover, the accumulative release amount at 24 h of the former was significantly lower (<90%) and the residue amount was greater (>10%). As the angle θ1 and ratio L1/r increased, drug residues were reduced continuously, and began to be less than 10% from 120° (0.27), and less than 5% from 130° (0.36) and the accumulative release amount at 24 h was greater than 95%. When the angle θ1 was increased to 150° (0.58), the residue was 3.1%, and when the angle θ1 continued to increase to 180°, the changes of the release rates were very small, and the drug release had been nearly completed, and the residues were approximately constant. Considering that too large angle could probably make it difficult for the pressed tablet cores to be pushed off the molds, the angle θ1 was preferably 130° to 170°, most preferably 150°.

The tablets whose angle θ1 and ratio L1/r were 150° (0.58) were stored at room temperature for a long term, and the releases at different storage time were studied.
The results were shown in Table 39.

TABLE 39 the releases at different storage time

| storage time | sampling time (h) and release (%) | | | |
|---|---|---|---|---|
| | 4 h | 6 h | 12 h | 24 h |
| 0 month | 11.1 | 28.7 | 68.3 | 98.0 |
| 3 months | 9.2 | 26.1 | 63.3 | 96.4 |
| 6 months | 8.5 | 23.8 | 61.0 | 94.3 |
| 12 months | 8.0 | 22.1 | 59.9 | 92.5 |
| 24 months | 7.2 | 20.6 | 45.9 | 89.3 |

The experimental results showed that, Nifedipine controlled release tablets using semipermeable membrane materials cellulose acetate and polyethylene glycol (PEG) most commonly used in the prior art as film-forming materials and with the angle θ1 and ratio L1/r being 150° (0.58) exhibited a good release profile at the initial stage. After being stored for 6 months at room temperature, the release was reduced to certain extent. As time increased, the membrane aged seriously and the release was reduced more prominently, indicating that the combination of cellulose acetate and polyethylene glycol (PEG) resulted in aging. Athough the drug residues at the initial stage of release could be reduced by changing the angle θ1 and the ratio L1/r of the tablet cores, the release residues of samples tended to increase due to subsequently continuous aging of the semipermeable membrane, thus, there was still a potential stability risk.

Example 4C

Comparative Studies on the Release of Nifedipine Double-Compartment Osmotic Pump Controlled Release Tablets with Different Angle $\theta_1$ Using Semipermeable Membrane Materials According to the Present Invention 1. Formula
1.1 Formula of the tablet core (1000 tablets)

The Formula of the drug-containing layer of the tablet core was as same as Example 4B.

The Formula of the push layer of the tablet core was as same as Example 4B.

2. Formula of the coating solution

| composition | amount used (g) |
|---|---|
| ethyl cellulose N-100 | 30 |
| PVP k30 | 16 |
| ethanol (ml) | 1000 |

2 Preparation process

Preparation process of the coating solution for the semipermeable membrane was as follows:

A formulary amount of ethyl cellulose and PVP k30 were weighed, dispensed in ethanol, and then stirred to dissolve completely to obtain the coating solution.

The other steps of the preparation process were as same as Example 4B, wherein the weight increases of coating were 14.5-14.8%.

3 Determinaton of the release:
The determination method was as same as Example 4A, and the results were shown in Table 40.

TABLE 40 the release results of Example 4C

| | angle $\theta_1$ and the ratio $L_1/r$ as well as accumulative release (%) | | | | | | | |
|---|---|---|---|---|---|---|---|---|
| | 110° (0.18) | 120° (0.27) | 130° (0.36) | 140° (0.47) | 150° (0.58) | 160° (0.70) | 170° (0.84) | 180° (1.0) |
| weight increase % | 14.5 | 14.7 | 14.5 | 14.8 | 14.7 | 14.5 | 14.6 | 14.8 |
| sampling time   4 h | 9.3 | 9.5 | 10.3 | 11.5 | 11.3 | 10.7 | 12.1 | 11.8 |
| 6 h | 23.5 | 24.3 | 26.9 | 28.3 | 28.5 | 28.0 | 28.4 | 28.7 |
| 12 h | 60.8 | 62.2 | 64.3 | 67.9 | 68.1 | 67.5 | 67.0 | 70.5 |
| 24 h | 94.2 | 95.5 | 99.5 | 99.0 | 98.0 | 98.7 | 98.9 | 99.3 |
| content (%) | 101.7 | 101.3 | 102.4 | 101.3 | 99.8 | 100.6 | 101.7 | 101.3 |
| residue amount (%) | 7.5 | 5.8 | 2.9 | 2.3 | 1.8 | 1.9 | 1.8 | 2.0 |

It could be seen from the results that, the results obtained by using semipermeable membrane materials according to the present invention were similar to those of Example 4B. As the angle θ1 increased, drug residues were reduced continuously. After the angle θ1 and the ratio L1/r was increased to 150° (0.58), the decrease of the release residue was not obvious, and the drug release had been nearly completed. After comprehensive consideration, the optimal value of the angle θ1 and the ratio L1/r is determined as 150° (0.58). Under same conditions, the release rates of the tablets whose angle θ1 and ratio L1/r were 110° (0.18) were significantly slower than those of the tablets whose angle θ1 and ratio L1/r were 150° (0.58). Moreover, the accumulative release amount at 24 h was significantly lower and the residue amount was greater.

In addition, when the above results were compared with those of Example 4B using cellulose acetate and PEG 6000 as semipermeable film forming materials, it could be seen that, when the two kinds of tablets were just prepared, in the case of larger angle θ1 and ratio L1/r, the residues of the tablets using semipermeable membrane materials according to the present invention and the tablets in Example 4B were both very low. However, in the case of smaller angle θ1 and ratio L1/r, the residue amount of the tablets in Example 4B was greater.

The above tablets whose angle θ1 and ratio L1/r was 150° (0.58) were stored at room temperature for a long term, and the releases were determined at different storage time. The results were shown in Table 41.

TABLE 41 the releases at different storage time

| | sampling time (h) and release (%) | | | |
|---|---|---|---|---|
| storage time | 4 h | 6 h | 12 h | 24 h |
| 0 month | 11.3 | 28.4 | 67.1 | 98.5 |
| 3 months | 11.2 | 28.2 | 66.9 | 98.1 |
| 6 months | 10.7 | 27.8 | 67.0 | 98.2 |
| 12 months | 11.2 | 29.0 | 66.9 | 97.8 |
| 24 months | 11.3 | 28.7 | 68.5 | 99.3 |

The experimental results showed that, compared with Example 4B, the membrane of the tablets using semipermeable film forming materials according to the present invention did not age during long term storage, and the release residue did not increase.

In conclusion, it could be seen from the above experimental results that, for double-compartment osmotic pump controlled release tablets, the tablets using film-forming materials of the present invention for semipermeable film and with larger angle θ1 and ratio L1/r for the drug-containing layer could not only reduce the release residues of the controlled release tablets, but also effectively ensure that the release residues do not increase after long-term storage.

Example 5

Comparative Studies on Different Shapes (Symmetric and Asymmetric) of Nifedipine Controlled Release Tablets Using the Film-Forming Materials According to the Present Invention for the Semipermeable Membrane 1. Formula (1000 tablets)

Formula of the drug-containing layer of the tablet core: as same as that of Example 4B Formula of the push layer of the tablet core: as same as that of Example 4B Formula of the coating solution: as same as that of Example 4C

| composition | amount used |
|---|---|
| ethyl cellulose N-100 | 30 g |
| PVP k30 | 16 g |
| ethanol | 1000 ml |

2. Peparation process

The operating steps are as same as Example 4C. When pressing, the angle θ1 and L1/r of the drug-containing layer and the angle θ2 and L2/r of the push layer for symmetric tablet core were both 135° (0.41), and the weight increase after coating was 14% and 15.4%, respectively, however, the angle θ1 and L1/r of the drug-containing layer was 135° (0.41), and the angle θ2 and L2/r of the push layer for asymmetric tablet core were 110° (0.18), and the weight increase after coating was 14.2% and 15.1%, respectively 3. Determination of the release:

The determination method was as same as Example 4A. The results were shown in Table 42.

TABLE 42

The release determination results of Example 5

| shape | weight increase | sampling time (h) and release (%) | | | |
|---|---|---|---|---|---|
| | | 4 h | 6 h | 12 h | 24 h |
| symmetric | 14.0% | 10.8 | 25.2 | 66.1 | 100.3 |
| | 15.4% | 10.1 | 23.7 | 63.0 | 99.2 |
| asymmetric | 14.2% | 11.8 | 27.4 | 65.6 | 99.8 |
| | 15.1% | 12.3 | 25.6 | 65.0 | 100.1 |

It can be seen from the results that, when the angle θ1 and L1/r for the drug-containing layers were equal, the releases of the symmetric osmotic pump tablets and the asymmetric osmotic pump tablets were similar, indicating that the effects of the angle θ2 formed between the push layer and the lateral surface and the height ratio L2/r on the release of the osmotic pump preparation were very small.

The release determination results of the asymmetric Nifedipine controlled release tablets with 15.1% weight increase after coating after long term storage at room temperature were shown in Table 43 below:

TABLE 43

The release determination results after long term storage at room temperature

| | sampling time (h) and release (%) | | | |
|---|---|---|---|---|
| storage time | 4 h | 6 h | 12 h | 24 h |
| 0 day | 12.3 | 25.6 | 65.0 | 100.1 |
| 6 months | 11.8 | 24.3 | 63.5 | 99.2 |
| 12 months | 11.4 | 23.7 | 62.9 | 99.7 |
| 24 months | 10.9 | 22.5 | 63.0 | 99.0 |

The results after long term storage at room temperature showed that the release property had little change and the release residues were substantively not increased during the storage period.

The experimental results of this example showed that, the use of new semipermeable film-forming materials and the larger angle θ1 and the ratio L1/r of the drug-containing layer of the present invention at the same time can not only reduce the released residues of the controlled release tablets, but also effectively ensure the release residues are substantively not increased or age, and the release is complete after long-term storage, so no excessive feeding is required.

What is claimed is:

1. An oral osmotic pump controlled release tablet comprising ethyl cellulose and povidone as film forming materials of a semipermeable membrane, the osmotic pump controlled release tablet including a tablet core, a semipermeable membrane and an optional film coating layer, wherein the weight ratio of ethyl cellulose and povidone is 1:1 to 4:1; and wherein the tablet core comprises a drug-containing layer and a push layer, wherein:
   (1) an angle θ1 formed by an outer curved surface of the drug-containing layer and a lateral surface of the drug-containing layer is 130°-180°, and an angle θ2 formed by an outer curved surface of the push layer and a lateral surface is 95°-120°, and
   (2) a ratio of L1/r is 0.36-1.0, wherein L1 is a vertical distance from a central vertex of the outer curved surface of the drug containing layer to a plane formed by an intersection line between the outer curved surface of the drug containing layer and the lateral surface, and r is a radius of the tablet core, and a ratio L2/r is 0.04-0.27, wherein L2 is a vertical distance from a central vertex of the outer curved surface of the push layer to a plane formed by an intersection line between the outer curved surface of the push layer and the lateral surface, and r is a radius of the tablet core.

2. A method for preparing the oral osmotic pump controlled release tablet of claim 1, wherein said method comprises coating the semipermeable membrane on the tablet core.

3. The oral osmotic pump controlled release tablet according to claim 1, wherein the angle θ1 is 130° to 170°, and the ratio L1/r is 0.36-0.84.

4. The oral osmotic pump controlled release tablet according to claim 1, wherein the angle θ1 is about 150°, and the ratio L1/r is about 0.58.

5. The oral osmotic pump controlled release tablet according to claim 1, wherein the angle formed by the outer curved surface of the drug-containing layer and the lateral surface is about 150°, and the ratio L1/r is about 0.58.

6. The oral osmotic pump controlled release tablet according to claim 1, wherein a pushing agent for the push layer is selected from the group consisting of methyl cellulose, hydroxypropyl cellulose, hypromellose, polyethylene, carbomer, sodium carboxymethyl starch, carboxymethyl cellulose or sodium salt thereof, cross-linked carboxymethyl cellulose sodium, and a combination thereof.

\* \* \* \* \*